United States Patent [19]

Baker et al.

[11] Patent Number: 4,513,005
[45] Date of Patent: Apr. 23, 1985

[54] SRS-A ANTAGONISTS

[75] Inventors: Stephen R. Baker, Eversley; William B. Jamieson, Woking; William J. Ross, Lightwater; Alec Todd, Wokingham, all of England

[73] Assignee: Lilly Industries Limited, London, England

[21] Appl. No.: 386,570

[22] Filed: Jun. 9, 1982

[30] Foreign Application Priority Data

Jun. 18, 1981 [GB] United Kingdom ............... 8118720
May 7, 1982 [GB] United Kingdom ............... 8213211

[51] Int. Cl.³ ............... C07C 149/20; A61K 31/335; A61K 31/23
[52] U.S. Cl. ............... 514/451; 260/402.5; 549/292; 562/426; 562/427; 514/459; 514/477; 514/478; 514/484; 514/547; 514/549; 514/558; 514/560
[58] Field of Search ............... 260/402.5; 549/292; 424/308, 309, 312, 279; 562/426, 427

[56] References Cited

U.S. PATENT DOCUMENTS 4,311,645 1/1982 Rosenberger ............... 260/348.61
4,352,757 10/1982 Gleason et al. ............... 549/513

FOREIGN PATENT DOCUMENTS 57-118555 7/1982 Japan.

OTHER PUBLICATIONS

*Tetrahedron Letters,* 22 (49) 4933; (26), 2505; (1981).
*Tetrahedron Letters,* 23 (10), 1023; (2), 167; (1982).
Jeffrey L. Fox, *Chemical and Engineering News,* 57 (24), 19 (Jun. 11, 1979).
*Proc. Natl. Acad. Sci. USA,* 76 (9), 4275 (1979).
*J. Am. Chem. Soc.,* 101 (22), 6748 (1979).
*Biochemical and Biophysical Research Communications,* 91 (4), 1266 (1979).
*J. Am. Chem. Soc.,* 102 (4), 1436; 5425; (1980).
*Tetrahedron Letters,* 21, 3143; 4123; (1980).
*Prostaglandins,* 19 (5), 645 (1980).
*Journal of Biological Chemistry,* 255 (15), 7093 (1980).
*Biochemical and Biophysical Research Communications,* 103 (4), 1258 (1981).
*Proc. Natl. Acad. Sci. USA,* 78 (7), 4579; (5), 3195; (1981).
The International Symposium on Leukotrienes and Other Lipoxygenase Products, held in Florence, Italy on Jun. 10-12, 1981, Abstract, p. 22.
*Ibid,* p. 37.
*Ibid,* p. 77.
*Advances in Prostaglandin, Thromboxane, and Leukotriene Research,* vol. 9, Leukotrienes and Other Lipoxygenase Products (Raven Press, New York), pp. 223-227 (1982).

*Primary Examiner*—Thomas A. Waltz
*Attorney, Agent, or Firm*—Charles W. Ashbrook; Arthur R. Whale

[57] ABSTRACT

There are described pharmacologically active compounds, useful in the treatment of allergic/inflammatory disorders involving SRS-A as causal mediator and which, in free acid form, are of formula I,

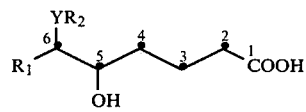

in which $R_1$ is (i) an aliphatic, saturated or unsaturated hydrocarbyl radical of up to 20 carbon atoms, unsubstituted or substituted by at least one substituent selected from halogen, hydroxy, $C_{3-6}$ alkoxy, $C_{3-6}$ cycloalkyl, aryl or heteroaryl, the cycloalkyl, aryl or heteroaryl being unsubstituted or substituted by at least one substituent selected from hydroxy, halogen and alkyl, alkenyl or alkynyl of up to 10 carbon atoms, (ii) cycloalkyl of 3 to 8 carbon atoms unsubstituted or substituted by alkyl, alkenyl or alkynyl of up to 16 carbon atoms, or (iii) aryl or heteroaryl, unsubstituted or substituted by hydroxyl, $C_{1-4}$ alkoxy, halogen or alkyl, alkenyl or alkynyl of up to 16 carbon atoms; and $R_2$ is (i) alkyl, cycloalkyl or alkenyl of up to 10 carbon atoms, unsubstituted or substituted by one or more substituents selected from aryl, cycloalkyl, halogen, hydroxy, $NHR_3$ and COX, where $R_3$ is H, $C_{1-4}$ alkyl, aryl or an amino acid residue or COX, and X is OH, $C_{1-4}$ alkyl, $NH_2$ or an amino acid residue, or (ii) aryl or heteroaryl, unsubstituted or substituted by one or more substituents selected from $C_{1-4}$ alkyl, $C_{1-4}$ alkoxy, $C_{2-5}$ acyl, halogen, hydroxy, carboxy, nitro, trihalomethyl, phenyl, $C_{1-4}$ acylamino and $NHR_4$, where $R_4$ is hydrogen or $C_{1-4}$ alkyl; and Y is —S—, —SO— or —$SO_2$—, with the proviso that when —$YR_2$ is glutathionyl, cysteinyl or cysteinylglycinyl, then $R_1$ is other than an unsubstituted alkatetraenyl or alkapentaenyl radical of 12 to 16 carbon atoms.

9 Claims, No Drawings

SRS-A ANTAGONISTS

The invention relates to alkanoic acid derivatives.

The invention provides compounds which, in free acid form, are of formula I,

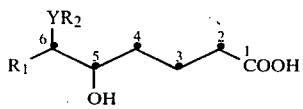

in which $R_1$ is (i) an aliphatic, saturated or unsaturated hydrocarbyl radical of up to 20 carbon atoms, unsubstituted or substituted by at least one substituent selected from halogen, hydroxy, $C_{3-6}$ alkoxy, $C_{3-6}$ cycloalkyl, aryl or heteroaryl, the cycloalkyl, aryl or heteroaryl being unsubstituted or substituted by at least one substituent selected from hydroxy, halogen and alkyl, alkenyl or alkynyl of up to 10 carbon atoms, (ii) cycloalkyl of 3 to 8 carbon atoms unsubstituted or substituted by alkyl, alkenyl or alkynyl of up to 16 carbon atoms, or (iii) aryl or heteroaryl, unsubstituted or substituted by hydroxyl, $C_{1-4}$ alkoxy, halogen or alkyl, alkenyl or alkynyl of up to 16 carbon atoms; and $R_2$ is (i) alkyl, cycloalkyl or alkenyl of up to 10 carbon atoms, unsubstituted or substituted by one or more substituents selected from aryl, cycloalkyl, halogen, hydroxy, $NHR_3$ and COX, where $R_3$ is H, $C_{1-4}$ alkyl, aryl, an amino acid residue or COX', X is OH, OR', $NH_2$, or an amino acid residue, X' is $C_{1-4}$ alkyl, $NH_2$, or an amino acid residue, and R' is $C_{1-4}$ alkyl, or (ii) aryl or heteroaryl, unsubstituted or substituted by one or more substituents selected from $C_{1-4}$ alkyl, $C_{1-4}$ alkoxy, $C_{2-5}$ acyl, halogen, hydroxy, carboxy, nitro, trihalomethyl, phenyl, $C_{1-4}$ acylamino and $NHR_4$, where $R_4$ is hydrogen or $C_{1-4}$ alkyl; and Y is —S—, —SO— or —$SO_2$—, with the proviso that when —$YR_2$ is glutathionyl, cysteinyl or cysteinylglycinyl, then $R_1$ is other than an unsubstituted alkatetraenyl or alkapentaenyl radical of 12 to 16 carbon atoms.

Preferred compounds are those of the above formula I in which $R_1$, $R_2$ and Y have the stated values, with the proviso that $R_1$ is other than an unsubstituted monoalkyl radical of $\leq 5$ carbon atoms or an unsubstituted alkatrienyl, alkatetraenyl, alkapentaenyl or alkadiendiynyl group of 12 to 16 carbon atoms.

In the above formula, the compounds are shown in free acid form. They also exist in lactone, salt and ester forms, which forms are embraced by the present invention. When in lactone form, their formula, as will be appreciated, is as follows

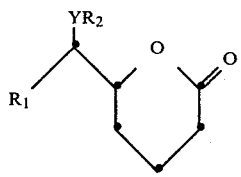

Of the salt forms, the pharmaceutically acceptable salt forms are preferred and as examples may be given the alkali and alkaline earth metal salt forms as well as ammonium and amine salt forms, the alkali metal, especially the sodium and potassium, salt forms being particularly preferred.

Of the ester forms, the pharmaceutically acceptable ester forms are preferred and as examples may be given the alkyl, silyl, cycloalkyl, cycloalkyl-alkyl and aralkyl ester forms, the $C_{1-4}$ alkyl ester forms being particularly preferred.

Since the compounds of formula I can contain more than one carboxylic acid group, so called partial salts and partial esters, i.e. compounds in which not all the carboxylic acid functions are in salt or ester form, are possible, as, indeed, are mixed salt/ester forms.

In the compounds of formula I, Y is preferably S or $SO_2$.

Where $R_1$ is an unsubstituted aliphatic or saturated hydrocarbyl radical, such is preferably a straight or branched chain alkyl radical of 2 to 18, preferably 5 to 16, carbon atoms, with the straight chain alkyl radicals being more preferred. Where $R_1$ is a substituted aliphatic saturated hydrocarbyl radical and the substituents are halogen, alkoxy or hydroxy, it is preferably again a straight or branched alkyl radical of 2 to 18, preferably 5 to 16, carbon atoms, again with the straight chain alkyl radicals being preferred. Where $R_1$ is a substituted aliphatic saturated hydrocarbyl radical and the substituents are cycloalkyl, aryl or heteroaryl, it is preferably a $C_{2-6}$ alkyl radical and preferably straight chain. Where the cycloalkyl, aryl or heteroaryl substituents are themselves substituted, the preferred substituents are alkyl, alkenyl or alkynyl of up to 10 carbon atoms, the alkenyl and alkynyl radicals containing up to four carbon-carbon double or triple bonds. The preferred aryl radicals are phenyl and naphthyl radicals, the preferred heteroaryl radicals being pyridyl and thiophene radicals. The most preferred substituents on the aryl and heteroaryl radical are alkyl and alkenyl radicals. Of the aryl and heteroaryl radicals, the former are preferred.

Where $R_1$ is an aliphatic unsaturated hydrocarbyl radical, it may be an alkenyl or alkynyl radical and may contain one or more, preferably up to five, double or triple carbon-carbon bonds anywhere along its length and may, indeed, contain a mixture of double and triple bonds, and can be branched or unbranched. Where unsubstituted or substituted by halogen, alkoxy or hydroxy, the unsaturated hydrocarbyl radical is preferably of 2 to 18, more preferably of 5 to 16 carbon atoms. Where substituted by an aryl or heteroaryl substituent, the alkenyl or alkynyl radical is preferably of 2 to 6 carbon atoms, the preferred aryl and heteroaryl radicals and the preferred substituents on such radicals being as given for when $R_1$ is an alkyl radical. Of the unsaturated hydrocarbyl radicals as $R_1$, the alkenyl radicals, containing up to 5 carbon-carbon double bonds, are preferred, most preferred being the unsubstituted such radicals. Where $R_1$ is aliphatic unsaturated it is most preferably of the form

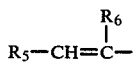

where $R_5$ is phenyl, benzyl, naphthyl or alkyl or monoalkenyl of 3 to 14 carbon atoms, and $R_6$ is hydrogen or $C_{1-4}$ alkyl.

Where $R_1$ is a cycloalkyl radical of 3 to 8 carbon atoms, such is preferably cyclopropyl, cyclopentyl or cyclohexyl. Any alkyl, alkenyl or alkynyl substituent on the cycloalkyl radical is preferably of up to 12 carbon atoms and any alkenyl or alkynyl substituent may contain more than one, preferably up to 5, carbon-carbon double or triple bonds.

As examples of aryl and heteroaryl radicals as $R_1$ may be given phenyl, naphthyl, pyridyl and thiophene radicals. Of the aryl and heteroaryl radicals, the former are preferred. The aryl or heteroaryl group can for example be substituted by hydroxyl, halogen or alkyl, alkenyl or alkynyl of up to 16 carbon atoms. Any alkyl, alkenyl or alkynyl substituent on the aryl or heteroaryl radical is preferably of up to 12 carbon atoms and any alkenyl or alkynyl substituent may contain more than one, preferably up to 5, carbon-carbon double or triple bonds. Of the substituted aryl and heteroaryl radicals as $R_1$, the preferred are those wherein the substituents are alkyl, alkenyl or alkynyl, particularly those where the substitutents are alkyl or alkenyl. Where $R_1$ is aryl the most preferred values are phenyl or naphthyl and when the aryl ring is substituted it preferably bears a single $C_{1-12}$ alkyl or phenyl group.

Where $R_2$ is unsubstituted alkyl or alkenyl, such is preferably of 2 to 5 carbon atoms and may be straight or branched, and when $R_2$ is cycloalkyl or is substituted by cycloalkyl, the cycloalkyl group preferably contains 3 to 8 carbon atoms. $R_2$ may, for example, be alkyl or alkenyl of up to 10 carbon atoms unsubstituted or substituted by one or more substituents selected from aryl, halogen, hydroxy, $NHR_3$ and COX, where $R_3$ is H, $C_{1-4}$ alkyl, aryl, an amino acid residue or COX', X is OH, OR', or an amino acid residue, X' is $C_{1-4}$ alkyl or an amino acid residue, and R' is $C_{1-4}$ alkyl. Any aryl substituent on an alkyl or alkenyl radical as $R_2$ is preferably phenyl. Where $R_2$ is substituted alkyl or alkenyl, the preferred substituents are $NHR_3$ and COX where $R_3$ is H, $C_{1-4}$ alkyl, aryl, an amino acid residue, or COX', X is OH or an amino acid residue and X' is $C_{1-4}$ alkyl or an amino acid residue. Preferred amino acid residues as $R_3$, X, or X' are glycine, glutamic acid, alanine and phenylalanine and when reference is made to an amino acid residue it is to be understood that the protected forms (protected with conventional groups) are also included. Of the alkyl and alkenyl significances of $R_2$, the former is preferred. Particularly preferred significances for the grouping —$YR_2$ are the peptide radicals glutathionyl, cysteinyl and cysteinylglycinyl of formulae

—SCH$_2$—CHCONHCH$_2$COOH ,
　　　　　|
　　　　NHCOCH$_2$CH$_2$CH(NH$_2$)COOH

—SCH$_2$CH(NH$_2$)COOH and —SCH$_2$CH(NH$_2$)CONHCH$_2$COOH, respectively.

Where $R_2$ aryl, such is preferably phenyl, and any substituent is preferably $C_{1-4}$ alkyl, $C_{1-4}$ alkoxy, halogen, hydroxy, carboxy or $NHR_4$. The substituents are also preferably electron withdrawing groups and in addition can be nitro, trihalomethyl especially trifluoromethyl, or $C_{2-5}$ acyl.

Any halogen in the compounds of formula I is preferably chlorine or bromine, particularly the former.

Particularly preferred significances of $R_1$ are as follows:

(a) unsubstituted $C_{5-16}$ alkyl or alkenyl, the alkenyl containing up to 5 double bonds,
(b) $C_{2-5}$ alkyl monosubstituted by phenyl,
(c) unsubstituted phenyl or naphthyl, and
(d)

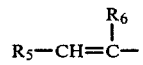

where $R_5$ is phenyl, benzyl, naphthyl or alkyl or monoalkenyl of 3 to 14 carbon atoms, and $R_6$ is hydrogen or $C_{1-4}$ alkyl.

Particularly preferred significances of $R_2$ are as follows:

(a) together with the sulphur atom in the grouping —$SR_2$, glutathionyl, cysteinyl and cysteinylglycinyl,
(b) phenyl, unsubstituted or substituted by one to three groups selected from $C_{1-4}$ alkyl, $C_{1-4}$ alkoxy, halogen, hydroxy or carboxy.

As will be appreciated, the compounds of formula I possess chiral centres at $C_5$ and $C_6$ and, accordingly, exist in the stereoisomeric forms 5R,6R; 5S,6S; 5R,6S and 5S,6R. Other chiral centres are also possible, depending on the nature of the substituents $R_1$ and $R_2$, leading to further stereoisomeric forms. Further, where the compounds contain alkenyl substituents, for example as or in $R_1$, cis-trans isomeric forms exist. It is not intended that the present invention be limited to any particular isomeric form.

Further instances of preferred groups of compounds are as follows:

(a) Compounds of the formula

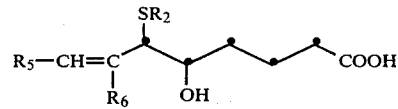

in which $R_2$ is alkyl, cycloalkyl or alkenyl of up to 10 carbon atoms, unsub-stituted or substituted by one or more substituents selected from aryl, cycloalkyl, halogen, hydroxy, $NHR_3$ and COX, where $R_3$ is H, $C_{1-4}$ alkyl, aryl, an amino acid residue or COX', X is OH, OR', $NH_2$, or an amino acid residue, X' is $C_{1-4}$ alkyl, $NH_2$, or an amino acid residue, and R' is $C_{1-4}$ alkyl, $R_5$ is alkyl or alkenyl of 3 to 14 carbon atoms, the alkenyl group being of formula $R_7CH=CH-$ where $R_7$ is $C_{1-12}$ alkyl, or phenyl or naphthyl, and $R_6$ is H or $C_{1-4}$ alkyl; and the lactone, salt and ester forms thereof.

It is preferred that $R_5$ is $C_{10-14}$ alkyl, especially $C_{11}$ alkyl, or $R_7CH=CH-$ where $R_7$ is $C_{8-12}$ alkyl, and the configuration of the $R_5$ group at the position 8 carbon atom can be Z or E configurations and is preferably Z.

The $R_2$ group can be a wide variety of radicals and is preferably $C_{2-5}$ alkyl substituted by one or more substituents selected from $NHR_3$ and COX where $R_3$ is H, an amino acid residue or COX', X is OH, OR', $NH_2$, or an amino acid residue, X' is $C_{1-4}$ alkyl, $NH_2$, or an amino acid residue, and R' is $C_{1-4}$ alkyl, such amino acid residues preferably being derived from glycine, alanine. A preferred formula for $R_2$ is

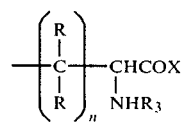

where each R is independently H or $C_{1-4}$ alkyl and n is 1 to 3, X is OH or OR' and $R_3$ is H or COR" where each of R' and R" is independently $C_{1-4}$ alkyl, preferably methyl.

Thus an especially preferred sub-generic group is of the formula

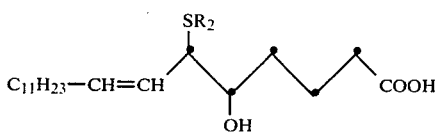

in which $R_2$ is

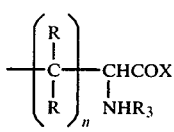

where each R is independently H or $C_{1-4}$ alkyl and n is 1 to 3, X is OH or OR' and $R_3$ is H or COR" where each of R' and R" is independently $C_{1-4}$ alkyl, preferably methyl.

Examples of $R_2$ groups include —$CH_2CH_2COOH$, $(CH_2)_5COOH$, —$CH_2CH(NH_2)COOH$,

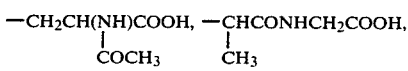

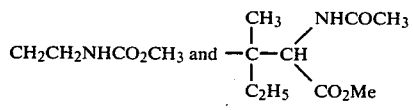

(b) Compounds of the formula

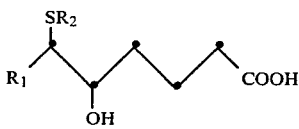

in which $R_1$ is substituted or unsubstituted phenyl or naphthyl or a group of the formula $R_5$—CH=CH where $R_5$ is phenyl, benzyl or naphthyl, and $R_2$ is unsubstituted or substituted phenyl; and the lactone, salt and ester forms thereof. When the $R_2$ substituent is substituted, the substituents may number up to 3 and are preferably chosen from $C_{1-4}$ alkyl, $C_{1-4}$ alkoxy, $C_{2-5}$ acyl, ($C_{1-4}$ alkyl CO) halogen, hydroxy, carboxy, nitro, trihalomethyl and $C_{1-4}$ acylamino, being most preferably halogen, trifluoromethyl or nitro.

An especially preferred sub-generic group has the formula

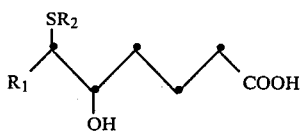

in which $R_1$ is naphthyl and $R_2$ is substituted phenyl preferably substituted with 1 to 3 halogen, nitro or trifluoromethyl groups.

(c) Compounds of the formula

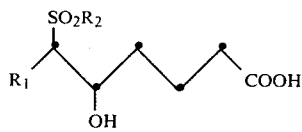

in which $R_1$ is a group of formula $R_5CH=CH—$ or $R_5CH_2CH_2—$ where $R^5$ is phenyl and $R_2$ is unsubstituted or substituted $C_{1-4}$ alkyl or unsubstituted or substituted phenyl; and the lactone, salt and ester forms thereof. Substituents on the phenyl nucleus can be any of those listed in (b) above.

The invention also provides a method for the production of the compounds of the invention, which process comprises (a) obtaining a compound which, in free acid form, is of formula I, above, in which Y is —S—, by (ai) reacting a compound which in free acid form is of formula II,

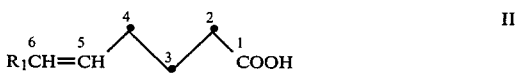

in which $R_1$ is as defined above, with a sulphenyl chloride of formula III, $R_2SCl$  III in which $R_2$ is as defined above, in an inert solvent and either isolating the resulting lactone form of the compound of formula I or hydrolysing the resulting lactone form to obtain a compound of formula I in free acid form; or (aii) reacting a compound which, in free acid form, is of formula IV,

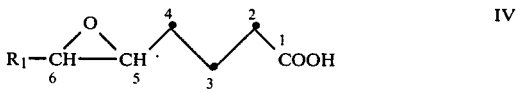

in which $R_1$ is as defined above, with a thiol of formula V, $R_2SH$  V in which $R_2$ is as defined above;

(b) obtaining a compound which in free acid form is of formula I, above, in which Y is —SO— or —$SO_2$— by oxidising a corresponding compound which in free acid form is of formula I above, but in which Y is —S—; or (c) obtaining a compound which in free acid form is of formula I, above, in which Y is —$SO_2$—, by reacting a compound of formula VI, $R_1$—$CH_2$—$SO_2R_2$  VI in which $R_1$ and $R_2$ are as defined above, with a compound which in free acid form is of formula VII;

and, where desired, isolating the resulting compound in free acid, lactone, salt or ester form.

Process (ai) is preferably carried out in the presence of a base, for example in the presence of an organic amine, preferably a tertiary organic amine, such as a trialkylamine, e.g. triethylamine. The reaction is carried out in an inert solvent such as in an ether, e.g. diethyl ether, or in a halogenated hydrocarbon, such as carbon tetrachloride. A suitable reaction temperature is from $-60°$ to $+60°$ C., preferably from $-20°$ to $+20°$ C. The initial product of the process is the lactone form of the compound of formula I which can be hydrolysed to the free acid form, for example using basic hydrolysis. This process (ai) is not preferred when compound II contains other double or triple bonds, e.g. when $R_1$ is an alkenyl grouping, since competing side reactions involving addition of the sulphenyl chloride at other than the $C_5$ double bond occurs. For these compounds process (aii) is preferred.

Because of the relative instability of the sulphenyl chloride of formula III, it is preferred for this reagent to be produced in situ, for example by chlorinating the corresponding thiol ($R_2SH$) or preferably the corresponding disulphide ($R_2S$—$SR_2$), employing, as chlorinating agent, molecular chlorine or sulphuryl chloride at a temperature of from $-60°$ to $+20°$ C. in an inert solvent, e.g. carbon tetrachloride.

The compounds II are preferably employed in free acid form.

The $C_5$ double bond in compounds II can be cis (Z) or trans (E), leading to different diastereoisomers of the final compounds.

Process (aii) is suitably carried out in the presence of a strong base (pKa>12) such as a trialkylamine, e.g. triethylamine and in an inert polar solvent such as in an alkanol, e.g. methanol. A suitable reaction temperature is from 10° to 50° C., preferably at room temperature. The reaction may be catalysed by adsorbing the thiol of formula V onto active alumina.

In the process (aii), it is preferred to employ compound IV in ester form, particularly in $C_{1-4}$ alkyl ester form and especially in the methyl ester form. The resulting compound of the invention will then initially be produced in corresponding ester form.

In this reaction, the isomeric 5-thio-6-hydroxy compound may be formed along with the desired 5-hydroxy-6-thio compound of formula I. The isomeric by-product can be removed from the mixture by formation of the acid form, followed by lactonisation, e.g. by heating in an inert solvent such as toluene, only the 5-hydroxy compound undergoing the lactonisation.

Process (b) can be carried out in conventional manner for the oxidation of a sulphide to a sulphoxide or sulphone, for example using a peroxy acid as oxidising agent. A particularly preferred oxidising agent is m-chloroperbenzoic acid. The reaction is suitably carried out in an inert solvent, such as in a halohydrocarbon, for example in methylene chloride. Where it is desired to obtain a sulphoxide, i.e. a compound of formula I in which Y is —SO—, it is preferred to use one mole of m-chloroperbenzoic acid per mole of sulphide of formula I at about 0° C. Where it is desired to obtain a sulphone, i.e. compound of formula I in which Y is —$SO_2$—, it is preferred to employ an excess of m-chloroperbenzoic acid at room temperature.

In this process it is preferred to employ the sulphide starting material of formula I in lactone form, resulting, initially, in production of the corresponding sulphone or sulphoxide in lactone form.

In process (c), it is preferred to employ the compound of formula VII in ester form, the preferred ester form being the methyl ester form, i.e. it is most preferred to employ methyl 4-formylbutyrate. The resulting compound of formula I is thereby obtained initially in corresponding ester form. The reaction is preferably carried out in the presence of a base, for example ethyl magnesium bromide, and in an inert solvent, such as in an aromatic hydrocarbon, e.g. benzene. Elevated reaction temperatures are preferred, e.g. at reflux.

The resulting compounds of the invention may be isolated and purified in conventional manner.

Interconversion as between the various forms of the compounds of the invention, e.g. salt, free acid, lactone and ester forms, may also be carried out in conventional manner. For example, ester forms can be converted into salt forms by treatment with the appropriate aqueous dilute base at a pH of from 9 to 10. The salt forms can be converted to the free acid forms by aqueous acidification. The free acid forms can be converted to the lactone forms by acid treatment at a pH of less than 5, and the salt or free acid forms can be converted to ester forms by base or acid catalysed esterification using an appropriate alcohol.

The intermediate compounds employed in the above processes (a) to (c) are either known or may be obtained from available starting materials in conventional manner.

For example, the compounds of formula II can be obtained by a Wittig reaction of 4-carboxybutyltriphenylphosphoniumbromide, of formula VIII,

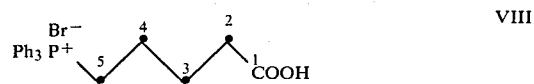

in which Ph signifies phenyl, with an aldehyde of formula IX,

in which $R_1$ is as defined above, in the presence of a strong base, such as sodium hydride in DMSO, or potassium tert-butoxide, a suitable reaction temperature being from 0° to 100° C., preferably from 10° to 30° C.

The sulphenyl chlorides of formula III may be prepared as described above when discussing process (ai), i.e. by chlorination of the coresponding thiols or disulphides.

The epoxides of formula IV, used in process (aii), above, can be prepared by oxidation of compounds of formula II, preferably in ester form, employing, for example, as oxidising agent, m-chloroperbenzoic acid or hydrogen peroxide. Where m-chloroperbenzoic acid is employed as oxidising agent, the oxidation is suitably carried out in chloroform, and, when hydrogen peroxide is employed, the oxidation is suitably carried out in methanol.

A particularly valuable and novel group of compounds which in free acid form are of formula IV are those which, in free acid form, are of formula $IV^1$

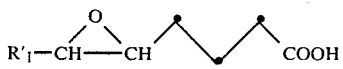

wherein $R_1'$ has the same significance as the $R_1$ values above, with the proviso that it is other than a $C_{12}$-$C_{16}$ alkatetraenyl or alkapentaenyl radical.

A preferred significance of $R_1'$ is a grouping of formula

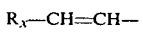

wherein $R_x$ is an aliphatic saturated or unsaturated hydrocarbyl radical of up to 18 carbon atoms, unsubstituted or monosubstituted by phenyl or naphthyl, each of which is unsubstituted or monosubstituted by alkyl, alkenyl or alkynyl of up to 10 carbon atoms, with the proviso that $R_x$ is other than an unsubstituted alkatrienyl or alkatetraenyl radical of 10 to 14 carbon atoms.

A further preferred group of intermedates is one in which $R_1'$ is of the formula

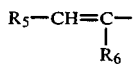

where $R_5$ is alkyl or alkenyl of 3 to 14 carbon atoms, the alkenyl group being of formula $R_7CH=CH-$ where $R_7$ is $C_{1-12}$ alkyl, or phenyl or naphthyl, and $R_6$ is H or $C_{1-4}$ alkyl.

A further preferred group of intermediates is one in which $R_1'$ is substituted or unsubstituted phenyl or naphthyl.

The compounds of formula VI, employed in process (c) can be prepared by reaction of a bromide of formula X,

in which $R_1$ is as defined above, with a sulphinate of formula XI,

in which $R_2$ is as defined above, suitably in dimethylformamide at room temperature.

The compounds of the present invention, i.e. compounds which in free acid form are of formula I, above, are pharmacologically active, being SRS-A antagonists as indicated in one or more of the following tests; the in vitro test on guinea pig ileum segments at concentrations of from 10 ng to 50 μg, according to the method of Schild, 1947 Brit. J. Pharm. 2 197–206 (the compounds of the invention as shown for instance in the following Examples exhibited an $IC_{50}$ against SRS-A of less than $10^{-4}$ molar); the in vivo Guinea Pig Pulmonary Function Test of Austen and Drazen 1974 J. Clin. Invest. 53:1679–1685 at intravenous dosage levels of from 0.05 μg to 5.0 mg/Kg and in a modified "Herxheimer" test at doses of from 25–200 mg/Kg. The "Herxheimer" test is based on an allergic bronchospasm induced in guinea pigs and which closely resembles an asthmatic attack in man. The mediators causing the bronchospasm are very similar to those released when sensitised human lung tissue is challenged with an antigen. In the modified test employed in respect of compounds of the present invention, the animals were pretreated with a histamine antagonist, mepyramine, at a dose of 0.5 mg/Kg i.p., 30 mins. before challenge. This modification masks the histamine effect to reveal better the SRS-A effect.

The compounds are accordingly indicated for therapeutic use in the treatment of allergic reactions of the pulmonary system where SRS-A is thought to be a causal mediator of bronchospasm, i.e. in allergic lung disorders such as extrinsic asthma and industrial asthmas such as Farmers lung and Pigeon Fanciers lung, as well as in other allergic/inflammatory or lung disorders where SRS-A is believed to be a mediator, such as allergic skin diseases, ectopic and atopic exzemas, psoriasis, contact hypersensitivity and angioneurotic oedema, bronchitis and cystic fibrosis.

The compounds may be administered in free acid form, in lactone form or in pharmaceutically acceptable salt or ester form. They may be administered by varous routes, for example by the oral or rectal route, by inhalation, topically or parenterally, e.g. by injection, being usually employed in the form of a pharmaceutical composition. Such compositions form part of the present invention and are prepared in a manner well known in the pharmaceutical art and normally comprise at least one active compound in association with a pharmaceutically acceptable diluent or carrier. In making the compositions of the present invention, the active ingredient will usually be mixed with a carrier, or diluted by a carrier, and/or enclosed within a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 10 mg to 1 g. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/Kg, more usually in the range of from 5 to 100 mg/Kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The following Examples illustrate the invention. In some instances it has not been possible to give a melting or boiling point, but it should be understood that all the compounds of the invention have been confirmed by physical methods.

EXAMPLE 1

(a) (Z)-8-Phenyl-5-octenoic acid

A stirred suspension of sodium hydride (12.0 g, 50% dispersion in oil) in dry dimethyl sulphoxide (100 ml) was heated to 70° to 75° C. under nitrogen for 40 minutes. The dark solution was cooled, a solution of 4-carboxybutyltriphenylphosphonium bromide (53 g) in dry dimethyl sulphoxide (100 ml) was added over 20 minutes at 20° to 25° C., and the solution was stirred for a further 10 minutes. 3-Phenyl-propionaldehyde (12.5 ml) was added with cooling to maintain a temperature of 30° to 35° C. and the mixture was stirred for a further 4 hours at room temperature, then poured on to ice-water (600 ml) and washed with chloroform. The aqueous phase was acidified and extracted with chloroform. The extract was washed with water, dried, and evaporated. The residual oil was distilled under vacuum to give the above product, b.p. 134° to 139° C./0.07 mm. $^{13}$C NMR spectroscopy showed the presence of about 5% (E)-isomer.

Following the procedure above and employing appropriate starting materials, 5-heptenoic acid[1], 65° to 71° C./0.3 mm (85% (Z), 15% (E) isomer by $^{13}$C NMR) and 5-undecenoic acid[2], b.p. 105° to 106° C./0.1 mm (90% (Z), 10% (E)) were similarly prepared:
1. J.C.S. (C) 217 (1968)
2. J.O.C. 43, 4387 (1978)

(b) (Z)-5-Hexadecenoic acid

A stirred suspension of 4-carboxybutyl-triphenylphosphonium bromide (44.8 g) in benzene (200 ml) was dried by heating under a water trap for 20 minutes. The mixture was cooled, solid potassium tert-butoxide (34.0 g) was added under nitrogen, and the stirred suspension was heated under reflux for 15 minutes. A solution of undecylic aldehyde (20.8 ml) in dry benzene (20 ml) was added to the cooled mixture at 20° to 25° C., and after stirring for a further 1 hour the mixture was diluted with ether and extracted with sodium chloride solution. The aqueous extract was acidified and reextracted with ether and the ether extract was dried and evaporated. Distillation of the residue gave the product b.p. 150° to 151° C./0.1 mm (90% (Z), 10% (E) by $^{13}$C NMR). (Chemical Abstracts 85: 159341 and Chem. Phys. Lipids 16, 215 (1976)).

(c) rel-(6R, 1'R)-6-(3'-Phenyl-1'-phenylthiopropyl)-tetrahydro-2H-pyran-2-one A solution of chlorine (0.9 g) in carbon tetrachloride (10 ml) was added dropwise to a stirred solution of diphenyl disulphide (2.2 g) in carbon tetrachloride (20 ml) at 0° to −5° C. The yellow solution was stirred for 10 minutes at 0° C. then a solution of (Z)-8-phenyl-5-octenoic acid (1.45 g), prepared as in (a) above, and triethylamine (0.93 ml) in carbon tetrachloride (20 ml) was added at 0° to −5° C. The mixture was stirred for 2 hours at room temperature then evaporated under vacuum. A solution of the residue in ether was washed with dilute hydrochloric acid, then with dilute sodium hydroxide solution, dried and evaporated to give a pale oil.

A solution of the crude neutral product in 10% sodium carbonate solution was heated under reflux for 2 hours, cooled, washed with ether, acidified and extracted with ether. The extract was dried and evaporated and a solution of the residual acid in toluene was heated under a water trap for 30 minutes and evaporated to give the crude lactone. This was further purified by chromatography on silica gel in ethyl acetate:petroleum spirit (1:3) to give the pure product.

(d) rel-(5R,6R)-5-Hydroxy-8-phenyl-6-phenylthiooctanoic acid

A stirred mixture of 6-(3-phenyl-1-phenylthiopropyl)-tetrahydro-2H-pyran-2-one (2.1 g), prepared as in (c) above, and 10% sodium carbonate solution (50 ml) was heated under reflux for 2 hours, cooled, diluted with sodium chloride solution, washed with ether, acidified and extracted with ether. The extract was dried and evaporated without heat to give the product as a pale oil.

(e) rel-(5R,6R)-5-Hydroxy-8-phenyl-6-phenylthiooctanoic acid, sodium salt

A solution of 5-hydroxy-8-phenyl-6-phenylthiooctanoic acid (1.45 g), prepared as above, in ethanol (50 ml) was made basic with molar sodium methoxide in methanol (4.1 ml) and the solution was evaporated to dryness under vacuum. The residue crystallised from isopropanol-petroleum spirit to give the title product m.p. about 150° C.

EXAMPLES 2 to 4

The lactones shown below were prepared by the method described in Example 1(c), employing appropriate starting materials and omitting the hydrolysis and re-lactonisation steps and purifying the products only by chromatography

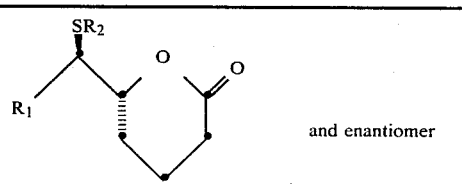

and enantiomer

| R$_1$ | R$_2$ |
|---|---|
| n-C$_{10}$H$_{21}$ | Ph |
| Ph(CH$_2$)$_2$ | 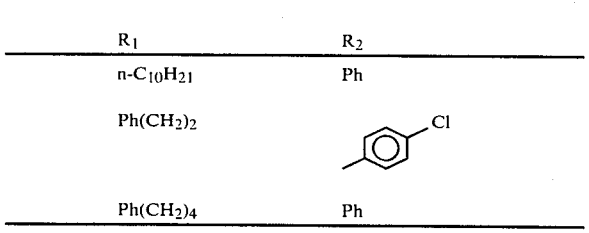 |
| Ph(CH$_2$)$_4$ | Ph |

These lactones were hydrolysed as described in Example 1(d) and converted as described in Example 1(e) to the sodium salts shown below:

[Structure: R1-CH(SR2)-CH=CH-CH=CH-CO2Na with OH, and enantiomer]

| R1 | R2 | Solvent of crystallisation | m.p. °C |
|---|---|---|---|
| n-C10H21 | Ph | freeze dried | — |
| Ph(CH2)2 | 4-Cl-C6H4 | iPrOH/petrol | ca 200 |
| Ph(CH2)4 | Ph | MeOH/iPrOH | — |

EXAMPLE 5

(a) (Z) And (E)-6-phenyl-5-hexenoic acids

A stirred suspension of 4-carboxybutyl-triphenylphosphonium bromide (38.2 g) in benzene (400 ml) was dried by heating under a water trap for 20 minutes. The mixture was cooled, solid potassium tert-butoxide (29.0 g) was added under nitrogen, and the stirred suspension was heated under reflux for 15 minutes. A solution of benzaldehyde (8.73 ml) in dry benzene (20 ml) was added to the cooled mixture at 20° to 25° C., and after stirring for a further 1 hour the mixture was diluted with ether and extracted with sodium chloride solution. The aqueous extract was acidified and re-extracted with ether and the ether extract was dried and evaporated. Distillation of the residue gave a mixture of (Z) and (E)-6-phenyl-5-hexenoic acids, b.p. 134° to 142° C./0.1 mm. This mixture was heated under reflux for 2 hours in methanol (250 ml) containing concentrated sulphuric acid (0.4 ml). The solution was evaporated and the residue was dissolved in ether, washed with sodium bicarbonate solution, dried and re-evaporated. The residue was distilled in a spinning band apparatus to separate methyl (Z)-6-phenyl-5-hexenoate, b.p. 122° to 123° C./0.3 mm, and the (E) isomer b.p. 133° C./0.3 mm.

A solution of methyl (Z)-6-phenyl-5-hexenoate (2.0 g) in dioxan (20 ml) and 10% sodium carbonate solution (20 ml) was heated under reflux for 6 hours and evaporated to low volume. The residue was diluted with water, washed with ether, acidified and extracted with ether. The extract was dried and evaporated to give (Z)-6-phenyl-5-hexenoic acid.

The (E)-isomer was similarly hydrolysed. (J.O.C. 31 1390 (1966)).

(b) rel-(5R,6R)-5-Hydroxy-6-phenyl-6-phenylthiohexanoic acid, sodium salt

A solution of chlorine (1.56 g) in carbon tetrachloride (23 ml) was added dropwise to a stirred solution of diphenyl disulphide (4.0 g) in carbon tetrachloride (50 ml) at 5° to 10° C. The yellow solution was stirred for 10 minutes at 5° to 10° C. then a solution of (Z)-6-phenyl-5-hexenoic acid (5.2 g) and triethylamine (3.8 ml) in carbon tetrachloride (50 ml) was added at 5° to 10° C. The mixture was stirred for 2 hours at room temperature then evaporated under vacuum. A solution of the residue in ether was washed with dilute hydrochloric acid, then with dilute sodium hydroxide solution, dried and concentrated to give crystals of 7-phenyl-6-phenylthio-2-oxepanone, m.p. 166° C. The mother liquor was evaporated and the residue was chromatographed on silica gel in ethyl acetate:petroleum spirit (1:3) to give an oil which crystallised from ether to give rel-(6R,αR)-6-(α-phenylthiobenzyl)-tetrahydro-2H-pyran-2-one, m.p. 82° to 84° C.

A stirred mixture of this 6-(α-phenylthiobenzyl)tetrahydro-2H-pyran-2-one (1.2 g), dioxan (10 ml) and 10% sodium carbonate solution (20 ml) was heated under reflux for 2 hours and then evaporated. A solution of the residue in water was washed with ether, acidified and extracted with ether. The extract was dried and evaporated and a solution of the residue in ethanol (50 ml) was made basic with molar sodium methoxide in methanol (3.8 ml) and evaporated to dryness under vacuum to give the title product, m.p. 210° C.

EXAMPLE 6 rel-(5R,6S)-5-Hydroxy-6-phenyl-6-phenylthiohexanoic acid, sodium salt

This compound, m.p. about 190° C., was prepared as described in Example 5, starting from the corresponding (E) isomer. The crude 6-membered lactone after chromatography was further purified by hydrolysis to the acid as described in Example 5(b) followed by heating in toluene under a water trap to re-lactonise. The toluene solution was evaporated and a solution of the residue in ethyl acetate was washed with 5% sodium carbonate solution, dried and evaporated. The residue crystallised from ether to give pure rel-(6R,αS)-6-(α-phenylthiobenzyl)-tetrahydro-2H-pyran-2-one, m.p. 126° C.

EXAMPLE 7

(a) Methyl (Z)-8-phenyl-5-octenoate

A solution of (Z)-8-phenyl-5-octenoic acid (12.6 g), see Example 1(a), and concentrated sulphuric acid (0.1 ml) in methanol (300 ml) was heated under reflux for 2 hours. The solution was evaporated and the residue distilled under vacuum to give the ester b.p. 110° to 113° C./0.1 mm.

(b) Methyl 5,6-oxido-8-phenyloctanoate

Solid m-chloroperoxybenzoic acid (10.7 g 80% purity) was added to a stirred solution of methyl (Z)-8-phenyl-5-octenoate (11.0 g), see (a) above, in chloroform (100 ml) at 15° to 20° C. The mixture was stirred for 4 hours at room temperature and filtered. The filtrate was washed with sodium bicarbonate solution, dried and evaporated and the residue was distilled under vacuum to give the product, b.p. 120° to 125° C./0.05 mm.

(c) 6-(R,S)-Ethylthio-5-(R,S)-hydroxy-8-phenyloctanoic acid

Ethanethiol (5.6 ml) was added dropwise to a stirred suspension of active (grade Super 1) alumina (150 g) in dry ether (160 ml). The suspension was stirred at room temperature for 5 minutes then a solution of methyl 5,6-oxido-8-phenyl-octanoate (4.8 g), see (b) above, in ether (40 ml) was added. The mixture was stirred for a further 1 hour, poured on to methanol (1 liter) and stirred for 2½ hours, and filtered. The filtrate was evaporated and the residue chromatographed to give a mixture of methyl 6-ethylthio-5-hydroxy-8-phenyloctanoate and methyl 5-ethylthio-6-hydroxy-8-phenyloctanoate as a pale oil.

A stirred mixture of this oil and 10% sodium carbonate solution (45 ml) was heated under reflux for 4 hours, cooled, washed with ether, acidified and extracted with ether. The extract was dried and evaporated and a solution of the residue in toluene (25 ml) was heated under a water-trap for 2 hours, diluted with ether, washed with sodium hydroxide solution, dried and evaporated. The residual lactone was stirred with 10% sodium carbonate solution (20 ml) with heating under reflux for 2 hours. The solution was washed with ether, acidified and extracted with ether and the extract was dried and evaporated to give the title product as a pale oil.

EXAMPLE 8

5-Hydroxy-8-phenyl-6-phenylthiooctanoic acid

This compound was prepared by the method described in Example 7(c) employing thiophenol in place of ethanethiol.

EXAMPLE 9

(a) Methyl 5,6 (E) oxido-7 (Z) nonadecenoate

Dodecyltriphenylphosphonium bromide (17.9 g) was dissolved in dry tetrahydrofuran (200 ml), stirred under nitrogen and cooled to −78° C. Butyl lithium (1.6 molar solution in hexane, 23 ml) was added gradually with formation of a deep orange colour. After stirring at −78° C. for 20 minutes, methyl 5,6 (E) oxido-7-oxoheptanoate (5.6 g) in tetrahydrofuran (20 ml) was added rapidly. The solution lightened in colour and was allowed to warm up to room temperature over 1 hour. The bulk of the solvent was evaporated in vacuo and the residue extracted with ether/hexane 50/50 v/v containing 1% triethylamine (3×30 ml). The bulked extracts were evaporated in vacuo to small volume and chromatographed on silica gel using the same solvent mixture. The fractions containing the title compound were bulked and evaporated in vacuo to give the product as a colourless oil at room temperature. After storage at −20° C. the product solidified.

(b) 5-(R,S) Hydroxy-6-(S,R)-S-cysteinyl-7(Z)-nonadecenoic acid

Methyl 5,6 (E) oxido-7(Z)nonadecenoate (1.62 g) was reacted with a solution of N-trifluoroacetylcysteine methyl ester (2.31 g) (protected form of a compound of formula V) and triethylamine (2.0 ml) in dry methanol (5.0 ml) at room temperature for 3 days. The solution was evaporated in vacuo and chromatographed on silica gel using dichloromethane/methanol 95/5 v/v as developing solvent to give the 6-fully protected cysteinyl derivative of the methyl ester of the title compound as a pale yellow oil.

This product (1.50 g) was dissolved in methanol (10 ml) and a solution of anhydrous sodium carbonate (0.8 g) in water (5 ml) was added with stirring. Additional water was carefully added to give a hazy solution which was stirred at room temperature for 3 days. The resultant clear solution at pH 10 was evaporated in vacuo to remove methanol and the aqueous residue adjusted to pH ca 5.5 with dilute hydrochloric acid followed by glacial acetic acid to pH ca 3. The mixture was extracted with dichloromethane and the dried (Na₂SO₄) extract evaporated in vacuo to give the title compound as a viscous colourless oil, which on storage at −20° C. slowly solidified.

EXAMPLES 10 TO 15

By repeating the procedure of Example 9(b), but employing appropriate starting materials there were obtained the following:

5-(R,S)-Hydroxy-6-(S,R)ethylthio-7(Z)-nonadecenoic acid 5-(R,S)-Hydroxy-6-(S,R)(2-carboxyethylthio)-7(Z)-nonadecenoic acid 5-(R,S)-Hydroxy-6-(S,R)S-(N-acetylcysteinyl)-7(Z)-nonadecenoic acid 5-(R,S)-Hydroxy-6-(S,R)-benzylthio 7(E)-9(E)/(Z)-11(E)/(Z)-14(Z)-eicosatetraenoic acid 5-(R,S)-Hydroxy-6-(S,R)-(2-aminoethylthio)-7(E)-9(E)/(Z)-11(E)/(Z)-14(Z)-eicosatetraenoic acid 5-(R,S)-Hydroxy-6-(S,R)-ethylthio 7(E)-9(E)/(Z)-11(E)/(Z)-14(Z)-eicosatetraenoic acid.

EXAMPLE 16

(a) (Z)-8-Phenyl-5-octenoic acid

A stirred suspension of sodium hydride (12.0 g, 50% dispersion in oil) in dry dimethyl sulphoxide (100 ml) was heated to 70° to 75° C. under nitrogen for 40 minutes. The dark solution was cooled, a solution of 4-carboxybutyltriphenylphosphonium bromide (53 g) in dry dimethyl sulphoxide (100 ml) was added over 20 minutes at 20° to 25° C., and the solution was stirred for a further 10 minutes. 3-Phenyl-propionaldehyde (12.5 ml) was added with cooling to maintain a temperature of 30° to 35° C. and the mixture was stirred for a further 4 hours at room temperature, then poured on to ice-water (600 ml) and washed with chloroform. The aqueous phase was acidified and extracted with chloroform. The extract was washed with water, dried, and evaporated. The residual oil was distilled under vacuum to give the above product, b.p. 134° to 139° C./0.07 mm. ¹³C NMR spectroscopy showed the presence of about 5% (E)-isomer.

(b) rel-(6R,1′R)-6-(3′-Phenyl-1′-phenylthiopropyl)tetrahydro-2H-pyran-2-one

A solution of chlorine (0.9 g) in carbon tetrachloride (10 ml) was added dropwise to a stirred solution of diphenyl disulphide (2.2 g) in carbon tetrachloride (20 ml) at 0° to −5° C. The yellow solution was stirred for 10 minutes at 0° C. then a solution of (Z)-8-phenyl-5-octenoic acid (1.45 g), prepared as in (a) above, and triethylamine (0.93 ml) in carbon tetrachloride (20 ml) was added at 0° −5° C. The mixture was stirred for 2 hours at room temperature then evaporated under vacuum. A solution of the residue in ether was washed with dilute hydrochloric acid, then with dilute sodium hydroxide solution, dried and evaporated to give a pale oil.

A solution of the crude neutral product in 10% sodium carbonate solution was heated under reflux for 2 hours, cooled, washed with ether, acidified and extracted with ether. The extract was dried and evaporated and a solution of the residual acid in toluene was heated under a water trap for 30 minutes and evaporated to give the crude lactone. This was further purified by chromatography on silica gel in ethyl acetate: petroleum spirit (1:3) to give the pure product.

(c) rel-(5R,6R)
5-Hydroxy-8-phenyl-6-phenylsulphonyl-octanoic acid

A solution of m-chloroperoxybenzoic acid (6.0 g, 85%) in dichloromethane (100 ml) was added dropwise to a stirred solution of rel-(6R,1'R) 6-(3'phenyl-1'-phenylthiopropyl)-tetrahydro-2H-pyran-2-one (4.2 g), in dichloromethane (200 ml) at 5° to 10° C. After 24 hours at room temperature the white solid which had precipitated (m-chlorobenzoic acid) was filtered. The filtrate was washed with 1% aqueous sodium sulphite, 5% aqueous sodium carbonate, and saturated sodium chloride solution, dried over anhydrous sodium sulphate, filtered and evaporated to afford rel (6R,1'R) 6-(1'-phenylsulphonyl-3'-phenylpropyl)-tetrahydro-2H-pyran-2-one as a colourless viscous oil which crystallised after chromatography (silica Sorbsil U 30) and trituration with diethyl ether m.p. 83° C.

The tetrahydropyran-2-one derivative (1.63 g) in 10% aqueous sodium carbonate (40 ml) was heated under reflux for 1 hour. The solution was cooled, washed with diethyl ether, acidified (to about pH2) and extracted with diethyl ether (50 ml). The extracts were washed with saturated aqueous sodium chloride solution, dried, filtered and evaporated to a colourless oil which crystallised on trituration with diethyl ether to give the title compound as a white solid m.p. 100° to 102° C.

EXAMPLE 17

Methyl 5-hydroxy-6-phenylsulphonyl-8-phenyl-octanoate

A solution of ethyl magnesium bromide (7.7 ml, 1.3M solution in diethyl ether) was added to a stirred solution of phenyl 3-phenylpropyl sulphone (2.6 g) in dry benzene (20 ml). The mixture was heated under reflux for ½ hour and then cooled to room temperature. Methyl formyl butyrate (1.3 g) was added and a white precipitate started to form. After 2 hours at room temperature iced water (70 ml) and 2 molar hydrochloric acid (20 ml) were added. The product was extracted into diethyl ether and then chromatographed (Sorbsil U 30 silica) to afford the title compound as a colourless viscous oil.

EXAMPLE 18

5-Hydroxy-8-phenyl-6-phenylsulphonyloctanoic acid

Methyl 5-hydroxy-8-phenyl-6-phenylsulphonyl-octanoate was hydrolysed with aqueous sodium carbonate as in the hydrolysis step of Example 16 to afford the title compound as a viscous oil.

EXAMPLES 19 TO 21

The following compounds were prepared as described in Examples 17 and 18.
5-Hydroxy-6-(4-chlorophenyl)sulphonyl-8-phenyl-octanoic acid
5-Hydroxy-6-(4-methylphenyl)sulphonyl-8-phenyl-octanoic acid
5-Hydroxy-6-phenylsulphonyl-8-phenyl-7-octenoic acid.

EXAMPLE 22

(a) (1-Naphthyl)methyl phenyl sulphone

A solution of 1-(chloromethyl)-naphthalene (17.6 g) in dimethyl formamide (20 ml) was added to a stirred suspension of sodium benzenesulphinate (16.4 g) in dimethyl formamide (80 ml). After 20 hours at room temperature the mixture was diluted with water and the white precipitate filtered. Recrystallisation from ethyl acetate-petroleum ether 60°–80° C. gave the title product, m.p. 89° C.

(b) 5-Hydroxy-6-(1-naphthyl)-6-phenylsulphonyl hexanoic acid, sodium salt

A solution of ethyl magnesium bromide (1.3M in diethyl ether) was added to a stirred solution of (1-naphthyl)methyl phenyl sulphone as prepared in (a) above (8.46 g) in dry tetrahydrofuran (80 ml) at −20° C. After 1 hour methyl formyl butyrate (7.8 g) was added at −20° C. The mixture was allowed to warm to 0° C. over 1 hour, poured into ice and hydrochloric acid and extracted into dichloromethane to give methyl 5-hydroxy-6-(1-naphthyl)-6-phenylsulphonyl hexanoate as a colourless viscous oil.

The methyl ester was hydrolysed by heating in dioxan (50 ml), water (45 ml) and with 2M aqueous hydrochloric acid (1 ml) for 8 hours to give the crude title compound. The product was purified by lactonisation, hydrolysis, and preparation of the sodium salt, m.p. about 170° C. (from iso-propyl alcohol).

EXAMPLE 23

(a) Cinnamyl ethyl sulphone

Hydrogen peroxide (30% w/w, 0.2 mol) was added to a stirred solution of cinnamyl ethyl sulphide (16.8 g) in acetic acid (100 ml). The mixture became hot (about 80° C., exothermic reaction) and was then heated to 100° C. for 2 hours. The mixture was then cooled, diluted with water, the precipitate filtered and recrystallised from carbon tetrachloride-petroleum ether 60° to 80° C. to give the title product, m.p. 100° C.

(b) 6-Ethylsulphonyl-5-hydroxy-8-phenyl-7-octenoic acid, sodium salt

The above compound was prepared from cinnamyl ethyl sulphone by the method described in Example 22(b) to give the product, m.p. about 130° C.

EXAMPLE 24

(a) 2-(Cinnamyl sulphonylpropyloxy)tetrahydropyran

Cinnamylthiopropionic acid, m.p. 87° C., was prepared from cinnamyl bromide and mercaptopropionic acid and oxidised by the method described in Example 23(a) to cinnamylsulphonylpropionic acid, m.p. 160° C. This acid was reduced by addition to a stirred suspension of lithium aluminium hydride (2 equivalents) in tetrahydrofuran at −20° to −25° C. and the product formed isolated by ethyl acetate extraction to give cinnamyl 3-hydroxypropyl sulphone, m.p. 86° C. A solution of cinnamyl 3-hydroxylpropyl sulphone, para-toluene sulphonic acid (catalytic) and dihydropyran (2 equivalents) in dichloromethane was allowed to stand at room temperature for 24 hours, evaporated, and recrystallised from diethyl ether to give the title compound, m.p. about 45° C.

(b) 5-Hydroxy-6-(3-hydroxypropylsulphonyl)-8-phenyl-7-octenoic acid, sodium salt 6-[1-(Hydroxypropylsulphonyl)-3-phenyl-2-propenyl]-tetrahydro-2H-pyran-2-one was prepared from 2-(cinnamyl sulphonylpropyloxy)tetrahydropyran by the method described in Example 22(d) and hydro-

EXAMPLE 25

6-(Carboxyethylsulphonyl)-5-hydroxy-8-phenyl-7-octenoic acid, disodium salt

A mixture of 6-[1-(hydroxypropylsulphonyl)-3-phenyl-2-propenyl]tetrahydro-2H-pyran-2-one, (see Example 24) (1.0 g) and pyridinium dichromate (4.67 g) in dimethyl formamide (10 ml) was stirred at room temperature for 20 hours. The mixture was diluted with water and extracted with ethyl acetate to give 6-[1-(carboxyethylsulphonyl)-3-phenyl-2-propenyl]tetrahydro-2H-pyran-2-one as an oil. The lactone was hydrolysed and the disodium salt prepared, as described in Example 22(b) to give the disodium salt of the title compound, m.p. about 203° C.

EXAMPLE 26

(a) 7-Methyl 5,6 (E) oxido-7-(E)/(Z) nonadecenoic acid methyl ester

Methyl formylbutyrate (13 g) and 1-triphenylphosphoranylidene-2-propanone (31.4 g) were refluxed together in toluene (200 ml) for 30 minutes. The toluene was then evaporated off and ether (200 ml) added to the residue to give a suspension which was stirred at room temperature for 5 minutes. The suspended triphenylphosphine oxide was filtered off and washed with a further 100 ml of ether. The combined ether solutions were evaporated to dryness to give a yellow oil which was distilled at 0.1 mm Hg using a Kugelrohr apparatus (air bath temperature 140° C.) to yield 7-oxo-5-octenoic acid methyl ester as a colourless oil.

Sodium bicarbonate (5 g) was dissolved in water (100 ml) and 50% aqueous hydrogen peroxide (5 ml) added. To this stirred solution at room temperature was added 7-oxo-5-octenoic acid methyl ester (3.4 g) in methanol (10 ml). After 100 minutes the resultant clear solution was extracted four times with dichloromethane (4×50 ml). The combined extracts were then dried (MgSO4) and evaporated to yield 7-oxo-5,6(E) oxido-5-octenoic acid methyl ester.

n-Dodecyl triphenyl-phosphonium bromide (11.02 g) was dissolved in dry tetrahydrofuran (100 ml) and the stirred solution cooled to −78° C. n-Butyl lithium (13.3 ml, 1.5M in hexane) was added to give an orange solution of the ylid which was stirred for 10 minutes at −78° C. prior to the addition of 7 oxo-5,6(E) oxido-5-octenoic acid methyl ester (3.7 g) in dry tetrahydrofuran (20 ml). The reaction mixture was then allowed to warm up to room temperature over a period of 1 hour. The tetrahydrofuran was evaporated off and ether (200 ml) added to the oily solid. After stirring for 1 hour, the ether was decanted off and the process repeated twice more. The combined ether extracts were evaporated to dryness to give a pale yellow oil which was chromatographed on a silica column eluted with hexane:ether (1:1) to give a mixture of E and z isomers of 7-methyl-5,6(E)-oxido-7-nonadecenoic acid methyl ester.

(b) 5(R,S) Hydroxy-6(S,R) [(2-{N-acetylamino}-2-methoxycarbonyl-1-ethyl-1-methylethyl)thio]7(Z) methyl nonadecenoic acid sodium salt DL N Acetyl-β-mercaptoisoleucine methyl ester (219 mg) was dissolved in dry methanol (2 ml) and triethylamine (202 mg) added. This solution was then added to 7-methyl-5,6(E)-oxido-7-nonadecenoic acid methyl ester (338 mg) to give a pale yellow solution which was allowed to stand at 50° C. for 5 days. The solution was then evaporated to yield a pale yellow oil which was chromatographed on a silica column eluted with ether to give 5(S) hydroxy-6(R) [(2-{N-acetylamino}-2-methoxycarbonyl-1-ethyl-1-methylethyl)thio]7(Z)/(E) methyl nonadecenoic acid methyl ester and its 5R,6S isomer as a colourless oil. This diester was then hydrolysed by dissolving it in methanol (8 ml) and adding aqueous (1.0M) potassium carbonate solution (12 ml). The resultant turbid solution was then stirred at room temperature until clear (16 hours). The pH was then adjusted to 4 with aqueous (2M) hydrochloric acid and the solution extracted four times with dichloromethane (4×10 ml). The combined extracts were evaporated to dryness and the resultant oil chromatographed on a silica column eluted with dichloromethane:methanol (95:5) to give the title compound as its free acid. The sodium salt was prepared by reacting the free acid with 1 equivalent of aqueous sodium bicarbonate solution.

EXAMPLE 27

5(R,S)Hydroxy-6(S,R)[(2-{N-acetylamino}-2-carboxy-1-ethyl-1-methylethyl)thio]7(Z) methyl nonadecenoic acid disodium salt The half ester of Example 26 (100 mg) was dissolved in 2M lithium hydroxide (3 ml) and the solution allowed to stand at room temperature for 16 hours. The pH of the solution was then adjusted to 3 using 2M hydrochloric acid and extracted 3 times with dichloromethane (3×10 ml). The combined extracts were dried (MgSO4) and then evaporated to yield a viscous oil which was azetroped with benzene (20 ml) for 2 hours to provide the lactone of the title compound. This lactone was then purified by chromatography on a silica column eluted with dichloromethane:methanol:acetic acid (90:9:1). Finally the lactone was converted to the title compound by treatment with 2 equivalents of aqueous sodium bicarbonate solution.

EXAMPLE 28

(a)
rel-(6R,1′R)-6-[4-(Chlorophenylthio)undecyl]tetrahydro-2H-pyran-2-one

This compound was prepared by the method described in Example 1(c).

(b)
rel-(5R,6R)-6-(4-Chlorophenylthio)-5-hydroxyhexadecanoic acid, potassium salt The lactone of (a) above was hydrolysed as described in Example 1(d). The ether extract was neutralised with 1M potassium hydroxide in ethanol and the solution was evaporated. A solution of the residue in water was freeze-dried to give the title product as a gum.

EXAMPLE 29 rel-(5R,6R)-5-Hydroxy-6-(4-hydroxyphenylthio)-8-phenyl octanoic acid, sodium salt Boron tribromide (3.0 ml) was added dropwise to a stirred cooled solution of rel-(6R,1′R)-6-[1′-(4-methoxyphenylthio)-3-phenylpropyl]-tetrahydropyran-2-one (3.4 g), prepared by the method described in Example 1(c), in dichlormethane (100 ml). The dark solution was stirred for 7 hours at room temperature then treated with water (50 ml). The solvent layer was dried and evaporated and a solution of the residue in ether was extracted with sodium carbonate solution. The aqueous extract was acidified and re-extracted with ether and the ether extract was dried, neutralised with 1M sodium methoxide in methanol (7.0 ml) and evaporated. Treatment of the residual gum with isopropanol-petroleum spirit gave the title compound as a solid.

EXAMPLE 30

(a) Methyl (E)-8-phenyl-5-octenoate

A solution of bromine (4.3 ml) in dichloromethane (50 ml) was added dropwise to a stirred solution of triphenylphosphine (22.2 g) in dichloromethane (300 ml). The pale yellow solution was evaporated and the residual solid was suspended in dry benzene (300 ml). Methyl 5,6-oxido-8-phenyloctanoate (19.0 g) (see Example 7(b)) was added and the mixture was stirred for 4 hours and then evaporated. The residue was extracted with petroleum spirit (400 ml) and the extract was again evaporated to give methyl rel-(5R,6R)-5,6-dibromo-8-phenyloctanoate as an oil.

Zinc powder (27.4 g) was added to a stirred solution of this dibromo compound (27.4 g) in acetic acid (250 ml). The mixture was stirred for 30 minutes, diluted with water (750 ml) and extracted with petroleum spirit (3×400 ml). The extract was washed with sodium bicarbonate solution, dried and evaporated and the residue was distilled under vacuum to give the title compound, b.p. 110° to 113° C./0.2 mm (containing about 10% (Z) isomer by HPLC analysis).

(b) Methyl (E)-8-phenyl-5-octenoate (alternative method to (a) above)

Chlorine gas was passed into a stirred solution of methyl (Z)-8-phenyl-5-octenoate (14.6 g) in dichloromethane (250 ml) at −65° C. until the solution became pale yellow. The solution was allowed to warm to −20° C. then poured on to ice/sodium metabisulphite solution. The solvent layer was washed with water, then with sodium bicarbonate solution, dried and evaporated to give methyl rel-(5R,6S)-5,6-dichloro-8-phenyloctanoate as a pale oil.

A stirred solution of this dichloro compound and sodium iodide (100 g) in dry dimethyl formamide (500 ml) was heated at 146° to 149° C. for 2½ hours, poured on to ice/water and extracted with ether. The extract was washed with sodium metabisulphite solution, then with sodium chloride solution, dried and evaporated. The residue was distilled under vacuum to give the title compound (containing about 10% (Z) isomer).

(c) (E)-8-Phenyl-5-octenoic acid

A stirred solution of methyl (E)-8-phenyl-5-octenoate (13.6 g) in dioxan (125 ml) and 10% sodium carbonate solution (125 ml) was heated under reflux for 7 hours then evaporated. The residue in water was washed with ether, acidified and extracted with ether and the extract was dried and evaporated. The residue was distilled under vacuum to give the title compound, b.p. 150° to 153° C./0.2 mm.

(d) (E)-5-Hexadecenoic acid

A stirred mixture of undecyl-triphenyl-phosphonium bromide (45.7 g), methanol (300 ml) and 2M sodium hydroxide solution (300 ml) was heated at 50° C. for 3 hours and then concentrated under vacuum until the oily product solidified. The solid was washed with water, dried and recrystallised from petroleum spirit to give diphenyl-undecylphosphine oxide, m.p. 69° C.

1.6M n-Butyl lithium solution in hexane (56 ml) was added to a stirred solution of the phosphine oxide (31.0 g) in dry tetrahydrofuran (400 ml) at −40° to −45° C. under nitrogen. The deep orange solution was stirred for 10 minutes at −40° to −50° C., then a solution of valerolactone (9.0 g) in dry tetrahydrofuran was added. The pale solution was allowed to warm to room temperature, poured on to ice and extracted with ether. The extract was dried and evaporated and the residue was crystallised from ether-petroleum spirit to give 1-(5-hydroxypentanoyl)undecyl-diphenylphosphine oxide, m.p. 70° C.

A stirred solution of this compound (19.1 g) and sodium borohydride (1.0 g) in ethanol (200 ml) was heated under reflux for 2 hours. The solution was evaporated and a solution of the residue in water was extracted with ether. The extract was dried and evaporated and the residue was crystallised from ether-petroleum spirit to give erythro-1-(1,5-dihydroxypentyl)undecyldiphenylphosphine oxide, m.p. 87° C.

A stirred mixture of this diol (16.2 g) and sodium hydride (1.7 g, 50% dispersion in oil) in dry dimethylformamide (200 ml) was heated at 50° to 52° C. for 1½ hours, cooled, diluted with ice/water and extracted with ether. The extract was washed with sodium chloride solution, dried and evaporated to give (E)-5-hexadecenol as a pale oil, solidifying to a waxy solid at 0° C.

A solution of this alcohol (9.9 g) in acetone (150 ml) was oxidised with aqueous chromic acid/sulphuric acid (Jones reagent) at 20° to 22° C. The mixture was poured on to ice and extracted with ether. The extract was dried and evaporated and the residue was distilled under vacuum to give the title compound, b.p. 145° to 160° C./0.2 mm.

(e) Lactones

The lactones shown below were prepared by the method described in Example 1(c) employing (E) isomers of the compounds of formula II (see (a), (b), (c) and (d) above).

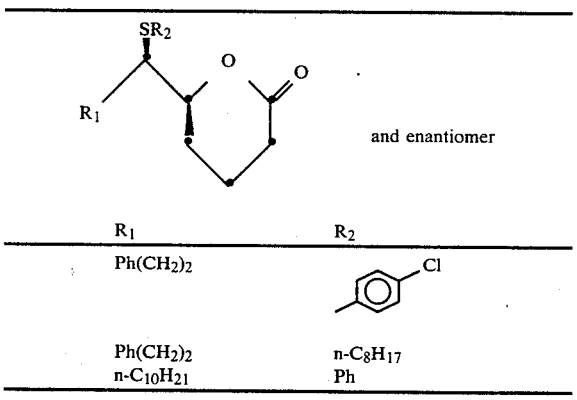

| R₁ | R₂ |
|---|---|
| Ph(CH₂)₂ | (4-Cl-phenyl) |
| Ph(CH₂)₂ | n-C₈H₁₇ |
| n-C₁₀H₂₁ | Ph |

EXAMPLES 31 TO 33

The lactones of Example 30 were hydrolysed as described in Example 1(d) and converted as described in Example 1(e) to the sodium salts shown below

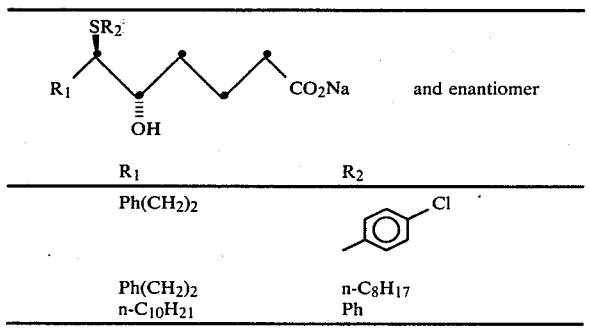

| $R_1$ | $R_2$ |
|---|---|
| Ph(CH$_2$)$_2$ | (4-Cl-C$_6$H$_4$) |
| Ph(CH$_2$)$_2$ | n-C$_8$H$_{17}$ |
| n-C$_{10}$H$_{21}$ | Ph |

EXAMPLE 34

(a) (Z) and (E)-6-(2-Naphthyl)-5-hexenoic acids

A stirred suspension of sodium hydride (24.0 g, 50% disperson in oil) in dry dimethyl sulphoxide (200 ml) was heated to 70° to 75° under nitrogen for 1 hour. The dark solution was cooled to 20° C., a solution of 4-carboxy-butyltriphenylphosphonium bromide (106 g) in dry dimethyl sulphoxide (200 ml) was added and the mixture was stirred for a further 10 minutes. A solution of 2-naphthaldehyde (31.2 g) in dry dimethyl sulphoxide (40 ml) was added with cooling to maintain a temperature of 25° to 30° C. and the mixture was stirred for a further 2 hours at room temperature then poured on to ice-water (1 L) and washed with chloroform. The aqueous phase was acidified and extracted with ether. The extract was dried and evaporated to give a mixture of (Z) and (E)-6-(2-naphthyl)-5-hexenoic acids which was esterified by the method described in Example 5(a) and the mixture of two methyl esters was partially separated by fractional distillation under vacuum.

The partially separated esters were hydrolysed as described in Example 5(a) and the acids were purified by crystallisation from ether-petroleum spirit to give (Z)-6-(2-naphthyl)-5-hexenoic acid, m.p. 66° C., and (E)-6-(2-naphthyl)-5-hexenoic acid, m.p. 95° C.

(b) Methyl (E)-6-(2-naphthyl)-5-hexenoate

A mixture of (Z) and (E) methyl esters prepared as described in (a) above was heated with 3-mercaptopropionic acid (few drops) at 150° to 160° C. for 20 hours, to give mainly (E) isomer. The product was distilled under vacuum, b.p. 150° to 162° C./0.1 mm. Methyl (E)-6-(4-biphenylyl)-5-hexenoate, m.p. 69° C., was similarly prepared.

(c) Methyl (E)-6-(1-naphthyl)-5-hexenoate

A mixture of (Z) and (E)-6-(1-naphthyl)-5-hexenoic acids was prepared and esterified by the method described in Example 5(a) and isomerised by the method described in (b) above to give the title compound b.p. 160° to 162° C./0.1 mm.

Methyl (E)-6-(4-octylphenyl)-5-hexenoate, b.p. 160° to 178° C./0.1 mm, was similarly prepared.

(d) Methyl (E)-6-(6-methyl-2-naphthyl)-5-hexenoate

A stirred solution of 2-bromomethyl-6-methyl-naphthalene (7.4 g) and triphenylphosphine (8.3 g) in toluene (200 ml) was heated under reflux for 8 hours. The solid product, (6-methyl-2-naphthyl)-methyl triphenylphosphonium bromide was filtered off and washed with ether, m.p. 270° C.

1.6M Butyl lithium solution in hexane (6.7 ml) was added to a stirred suspension of the phosphonium salt (5.0 g) in dry tetrahydrofuran (50 ml) at 5° C. under nitrogen. The dark solution was cooled to −50° C. and methyl 4-formylbutyrate (1.5 g) was added dropwise. The pale solution was stirred for 30 minutes at about −60° C., allowed to warm to −10° C., poured on to ice-sodium chloride solution and extracted with ether. The extract was washed with dilute hydrochloric acid, dried and evaporated and the residue was extracted with petroleum spirit to give a mixture of (Z) and (E) esters as an oil (2.8 g). Isomerisation by the method described in (b) above gave the title compound (2.1 g), m.p. 50° C.

(e) Methyl 6-(2-naphthyl)-5,6-oxidohexanoate

Solid m-chloroperoxybenzoic acid (15.3 g, 80% purity) was added to a stirred solution of methyl (E)-6-(2-naphthyl)-5-hexenoate (18.0 g) in chloroform (150 ml). The mixture was stirred for 2 hours at room temperature and filtered. The filtrate was washed with sodium bicarbonate solution, dried and evaporated and the residue was crystallised from ether.

The other epoxides shown below were prepared similarly using the (E) esters of (a) to (d) above. The products were not crystallised in every case.

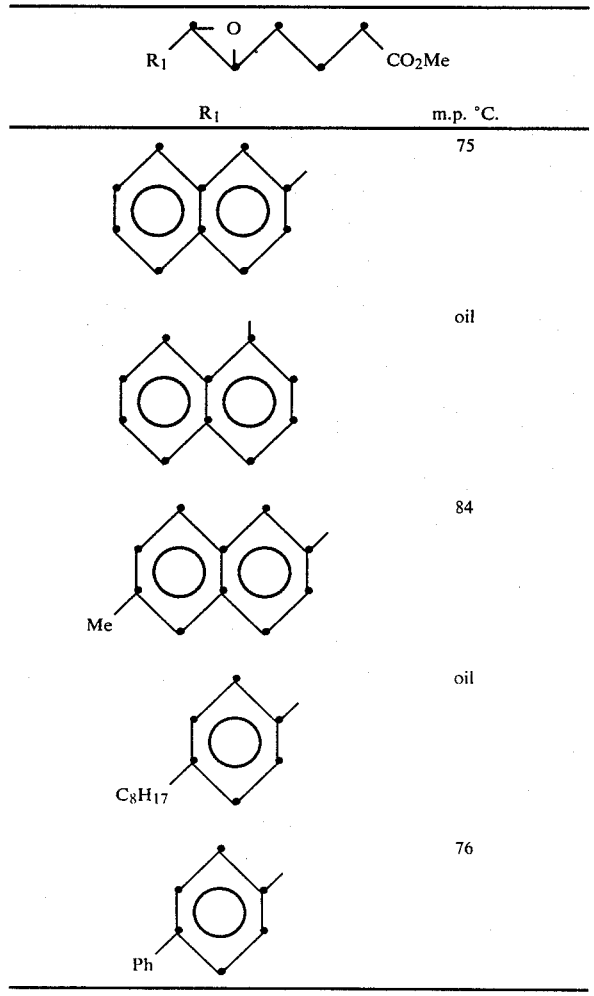

EXAMPLE 35

Methyl rel-(5R,6S)-5-hydroxy-6-(2-naphthyl)-6-phenylthiohexanoate

A mixture of methyl trans-5,6-oxido-6-(2-naphthyl)-hexanoate (0.27 g), thiophenol (0.2 ml) and triethylamine (0.5 ml) in methanol (4 ml) was stirred for 16 hours at room temperature under nitrogen. The clear solution was evaporated and the residue was chromatographed on silica-gel using 1:1 ether:petroleum spirit as developing solvent, to give the title compound, m.p. 90° C.

EXAMPLES 36 to 54

The esters shown below were prepared by the method described in Example 35.

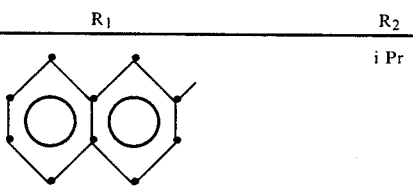

| R₁ | R₂ |
|---|---|

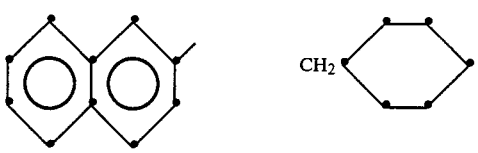

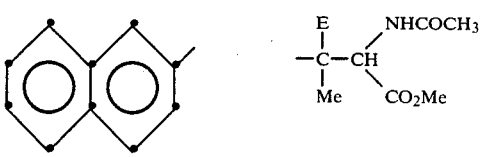

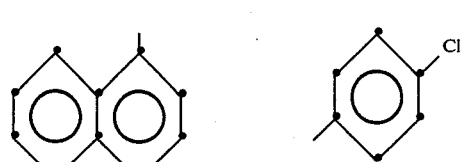

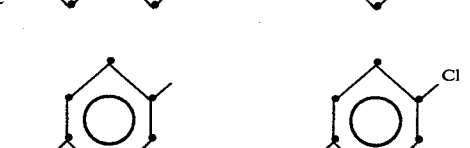

-continued

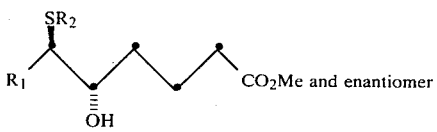

| R₁ | R₂ |
|---|---|

-continued

| SR₂ |
| R₁ ⋯⋯ CO₂Me and enantiomer |
| ŌH |

| R₁ | R₂ |
|---|---|
| Ph— | 4-OH, 3-COCH₃-phenyl |
| Ph— | 3-C₃H₇, 4-OH, 5-COCH₃-phenyl (approx.) |
| 4-C₈H₁₇-phenyl | 2,4,6-trichlorophenyl |
| 4-C₈H₁₇-phenyl | 4-CH₃-phenyl |
| 4-C₈H₁₇-phenyl | CH(NHCOCF₃)CO₂Me |

EXAMPLE 55 rel-(5R,6S)-5-Hydroxy-6-(2-naphthyl)-6-phenylthiohexanoic acid, sodium salt

A stirred mixture of the methyl ester (0.30 g, prepared as described in Example 35), 10% sodium carbonate solution (10 ml) and methanol (10 ml) was heated under reflux for 1½ hours. The methanol was evaporated under vacuum and the residue was diluted with water, washed with ether, acidified and extracted with ether. The extract was dried and evaporated and a solution of the residual acid in ethanol was basified with M sodium methoxide in methanol (0.75 ml) and re-evaporated. The residue solidified under isopropanol-petroleum spirit to give the title compound.

EXAMPLES 56 TO 72

The esters of Examples 36 to 53 were hydrolysed by the method described in Example 55 to give the sodium salts shown below.

| SR₂ |
| R₁ ⋯⋯ CO₂Na |
| ŌH and enantiomer |

| R₁ | R₂ |
|---|---|
| 2-naphthyl | 4-Cl-phenyl |
| 2-naphthyl | 2,4-Cl₂-phenyl |
| 2-naphthyl | 2,4,6-Cl₃-phenyl |
| 2-naphthyl | 4-CF₃-phenyl |
| 2-naphthyl | 3-NO₂, 5-CF₃-phenyl (approx.) |
| 2-naphthyl | 4-NHCOCH₃-phenyl |
| 2-naphthyl | iPr |
| 2-naphthyl | CH₂—cyclopropyl |
| 2-naphthyl (other position) | 4-Cl-phenyl |
| Me-naphthyl | 4-Cl-phenyl |
| Ph-phenyl | 4-Cl-phenyl |
| C₈H₁₇-phenyl | 4-Cl-phenyl |

-continued

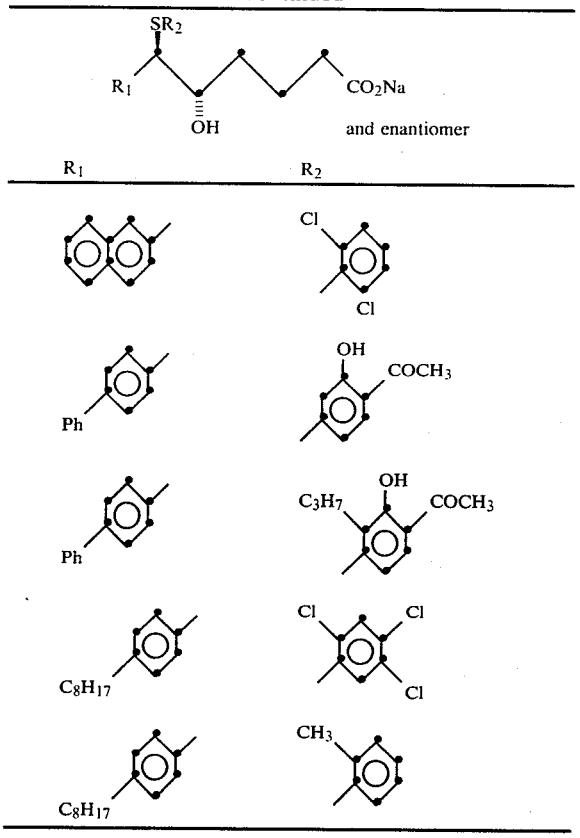

EXAMPLE 73 rel-(1'R,2'S)-S-5'-Carboxy-2'-hydroxy-1'-(4'octyl-phenyl)pentyl cysteine

A mixture of the diester of Example 54 (100 mg), 10% sodium carbonate solution (3 ml) and methanol (3 ml) was stirred at room temperature for 24 hours. The mixture was diluted with water, washed with ether, acidified to pH 4.0 and extracted with ethyl acetate. The extract was dried and evaporated to give the title product as a white solid.

EXAMPLE 74

2(R,S)-3(R,S)
rel-(1'R,2'S)-N-Acetyl-3-[5'-carboxy-2'-hydroxy-1'-(2-naphthyl)pentylthio]isoleucine methyl ester A solution of the diester (Example 44) (73 mg) in methanol (2 ml) and 1M potassium carbonate solution (1 ml) was stirred at room temperature for 20 hours, diluted with water, washed with dichloromethane, acidified and extracted with dichloromethane. The extract was dried and evaporated to give the title compound as a pale solid.

EXAMPLE 75

(a) (DL-N-acetyl-3-mercaptoisoleucyl)glycine methyl ester

Ethyl chloroformate (0.12 ml) was added to a stirred solution of DL-N-acetyl-3-mercaptoisoleucine (0.20 g) in dichloromethane (10 ml) and triethylamine (0.28 ml) at −10° C. The solution was allowed to warm to room temperature, washed with dilute hydrochloric acid and then with sodium bicarbonate solution, dried and evaporated to give 3-acetamido-4-ethyl-4-methyl-2-thietanone as a pale oil.

To a solution of this thiolactone in dichloromethane (5 ml) was added solid glycine methyl ester hydrochloride (0.15 g) and triethylamine (0.20 ml) and the mixture was stirred for 16 hours. The clear solution was washed with dilute hydrochloric acid and then with sodium bicarbonate solution, dried and evaporated and the residue was crystallised from methanol-water to give the title compound, m.p. 136° C.

(b)
5(S)-Hydroxy-6(R)-[(2-(N-acetylamino)-2-methoxycarbonyl-1-ethyl-1-methylethyl)thio]-7(Z)-nonadecenoic acid and its 5(R)-6(S)isomer Methyl 5,6(E)-oxido-7(Z)-nonadecenoate (162 mg) was reacted with a solution of DL-N-acetyl-β-mercaptoisoleucine methyl ester (216 mg) and triethylamine (200 μl) in dry methanol (500 μl) at 50° C. for 3 to 4 days. After blowing off the methanol in a stream of nitrogen the residue was dissolved in a mixture of diethylether/n-hexane 50/50 v/v and chromatographed on silica gel. Development with the same solvent mixture initially gave a recovery of unreacted epoxide. Further elution with a mixture of dichloromethane/methanol 95/5 v/v gave the required dimethyl ester, contaminated with a little of the free thiol, as a pale yellow oil.

The dimethyl ester was then dissolved in methanol (3 ml) followed by the addition of 2M sodium carbonate solution (1.5 ml) and a few drops of water to give a hazy solution. The hydrolysis was allowed to continue at room temperature for 3 days, after which time the nearly clear solution was carefully acidified to pH 3.5 (using dilute hydrochloric acid) and extracted with dichloromethane. The combined extracts were washed with water, dried over magnesium sulphate and evaporated in vacuo to give the title compound as a very pale yellow viscous oil.

EXAMPLE 76

5-(S)-Hydroxy-6(R)-[(2-(N-acetylamino)-2-carboxy-1-ethyl-1-methylethyl)-thio]-7(Z)-nonadecenoic-acid and its 5(R)-6(S)-isomer The monomethyl ester, from Example 75, (89 mg) was dissolved in tetrahydrofuran (4 ml) and 2M lithium hydroxide solution (1 ml) added, followed by further water (3 ml), to give a homogenous solution which was heated at 48° C. for 4 days. The tetrahydrofuran was then removed by evaporation in vacuo and the residue partitioned between dichloromethane and water at pH 3 (by adjustment with dilute hydrochloric acid). The dichloromethane extract was dried over magnesium sulphate and evaporated in a stream of nitrogen to give the desired dicarboxylic acid as a colourless viscous oil.

EXAMPLES 77 TO 85

(a)

The following thiol intermediates were prepared and converted to the end products in part (b) below by the method of Example 9(b).

(i) N-Trifluoroacetyl-L-cysteine carboxamide

The acid chloride of N-trifluoroacetyl L-cystine (1.0 g) was treated with 0.880 ammonia solution (5 ml) at 0° C. for 30 minutes. The excess ammonia was blown off and the clear solution diluted with a little water and shaken with diethyl ether. The resultant white solid was filtered off and dried.

This solid (0.25 g) was dissolved in dimethoxy ethane/water (5/2.5 ml), triphenylphosphine (0.25 g) added and the mixture stirred at room temperature for 16 hours. The solution was evaporated in vacuo to dryness and the residue dissolved in diethyl ether/ethyl acetate (2 ml, 90/10 v/v) and purified by chromatography on silica gel using the same solvent system, to give the desired thiol as a white crystalline solid.

(ii) N-(Mercaptoacetyl)alanine methyl ester

Dithiodiacetic acid (18.2 g) was dissolved in dry diethyl ether (150 ml), stirred and cooled to 0° C. Oxalyl chloride (18.5 ml) was added dropwise (also 2 drops of dimethylformamide added to catalyse the reaction). A steady stream of gas was produced and the mixture stirred at 0° C. for 1 hour, then for a further 1 hour at room temperature. The pale yellow solution was evaporated in vacuo to constant weight to give the acid chloride as a straw coloured liquid gradually darkening in colour.

A solution of the acid chloride (3.2 g) in dry tetrahydrofuran (20 ml) was added dropwise with stirring, to a solution of DL alanine methyl ester (5.3 g) in dry tetrahydrofuran (75 ml) at 0° C. A precipitate gradually formed and the mixture was stirred and reacted overnight at room temperature. The white precipitate was filtered off and discarded and the filtrate evaporated in vacuo to give the desired disulphide as a straw-coloured oil.

This product was dissolved in dimethoxyethane (20 ml) and added to a stirred solution of triphenylphosphine (3.5 g) in dimethoxyethane/water (20/10 ml). Reaction was complete after 4 hours at room temperature and the mixture was evaporated in vacuo to give a light straw-coloured oil. The product was dissolved in a little dichloromethane and chromatographed on silica gel using dichloromethane as solvent to remove excess triphenylphosphine. Continuing elution of the column with ethyl acetate gave the required thiol which, on evaporation of the eluants, was obtained as a pale yellow oil.

(iii) 2-(N-Methoxycarbonyl)aminoethane thiol

2-Aminoethane thiol hydrochloride (9.08 g) was stirred vigorously in ether (100 ml), cooled to 5° C. and 50% w/v sodium hydroxide solution added. Methyl chloroformate (6.5 ml) was added gradually whilst maintaining the temperature at <5° C. When half the chloroformate had been added, a solution of sodium hydroxide (3.2 g/25 ml water) was added simultaneously with the remaining chloroformate.

The mixture was stirred for 1 hour at 5° C., then the ether phase separated. The aqueous phase was further extracted with ether and the combined ether extracts washed with water, dried (MgSO$_4$) and evaporated in vacuo to give the title thiol and as a light straw-coloured oil.

(iv) N-Carboxamido L-cysteine

This thiol was prepared by the method described in German Pat. No. 1,518,734 (Chemical Abstracts 79:P137500p) Diamalt AG (Bayerlein F, et al).

(b) 5-(R,S)-Hydroxy-6-(S,R)-S-penicillaminyl-7(Z)-nonadecenoic acid

The final hydrolysis required 3 days at 40° C.:

5-(R,S)-Hydroxy-6-(S,R)-{1-[N-(carboxymethyl)carboxamido]ethylthio}-7(Z)-nonadecenoic acid 5-(R,S)-Hydroxy-6-(S,R)-cyclohexylmethylthio-7(Z)-nonadecenoic acid (the final hydrolysis required 12 hours at 50° C.)

5-(R,S)-Hydroxy-6-(S,R)-(5-carboxypentylthio)-7(Z)-nonadecenoic acid (the initial epoxide-thiol reaction required 24 hours at 50° C. as did the final hydrolysis)

5-(R,S)-Hydroxy-6-(S,R)-[(2-amino-2-carboxamido)ethylthio]-7(Z)-nonadecenoic acid 5-(R,S)-Hydroxy-6-(S,R)-[{2-amino-2-(N-ethylcarboxamido)}ethylthio]-7(Z)-nonadecenoic acid 5-(R,S)-Hydroxy-6-(S,R)-S-(N-carboxamido)cysteinyl-7(Z)-nonadecenoic acid 5-(R,S)-Hydroxy-6-(S,R)-[2-(N-methoxycarbonyl)aminoethylthio]-7(Z) nonadecenoic acid 5-(R,S)-Hydroxy-6-(S,R)-[N-(1-carboxyethyl)carboxamidomethylthio]-7(Z)-nonadecenoic acid.

EXAMPLES 86 AND 87

Decyltriphenylphosphonium bromide (4.26 g) was dissolved in dry tetrahydrofuran (60 ml), stirred under nitrogen and cooled to −78° C. Butyl lithium (1.6M solution in hexane, 6.2 ml) was added gradually with formation of a deep orange yellow colour. After stirring at −78° C. for 20 minutes, methyl 5,6(E) oxido-9-oxo-7(E) nonenoate (1.50 g) in tetrahydrofuran (8 ml) was added rapidly. The solution lightened in colour and was allowed to warm up to room temperature over 1 hour. Work up was continued as in Example 9(a) and the title compound was obtained as a colourless oil. This product became solid on storage at −20° C.

Reaction of this epoxide with various thiols under the conditions of Example 9(b) gave rise to the compounds listed below 5-(R,S)-Hydroxy-6-(S,R)-ethylthio-7(E),9(Z)-nonadecadienoic acid 5-(R,S)-Hydroxy-6-(S,R)-S-cysteinyl-7,9-nonadecadienoic acid.

EXAMPLE 88

(a) Methyl-5,6-(E)-oxido-8-phenyl-7(E,Z)-octenoate

To a stirred suspension of benzyl triphenylphosphonium chloride (33.43 g) is dry tetrahydrofuran (600 ml) under nitrogen at −70° C. (acetone/dry ice bath) was added n-butyl lithium (54 ml, 1.6 molar solution in hexane). A deep orange colour developed immediately. The mixture was stirred at −70° C. for 5 minutes. Then a solution of methyl-5,6-(E)-oxido-6-formyl-hexanoate (14.8 g) in dry tetrahydrofuran (30 ml) was added, and the reaction mixture allowed to warm gradually to room temperature (accompanied by partial discharge of ylid coloration to final straw yellow colour). Stirring at room temperature was continued for a further 1 hour when the reaction was shown to be complete by tlc.

The reaction mixture was evaporated in vacuo and extracted (3×) with diethyl ether. The extracts were evaporated in vacuo to yield an amber oil which was purified by column chromatography on silica (eluant hexane 50% dietyl ether 0.1% Et$_3$N) to give a light-yellow oil as the title compound.

(b)
5-(S,R)-Hydroxy-6-(R,S)-(succinylthio)-8-phenyl-7-(E,Z)-octenoic acid

To methyl-5,6-oxido-8-phenyl-7-(E,Z) octenoate (0.6 g), prepared as described in (a) above and a trace of hydroquinone under nitrogen, was added a mixture of triethylamine (0.54 g), dimethylmercaptosuccinate (0.87 g) and dry methanol, also under nitrogen.

The mixture was allowed to stand at room temperature for 2 hours and then blown down under a nitrogen stream. The residual oil was purified by column chromatography (silica; eluent dichloromethane 2% methanol 1% acetic acid) to give the tri-methyl ester of the title compound as a pale oil.

The above oil (320 mgs), was stirred in methanol 40 ml) with 0.1 molar potassium carbonate solution (136 ml) and a trace of hydroquinone for 72 hours at room temperature. The reaction mixture was acidified with glacial acetic acid and extracted with ethyl acetate to give an oil which was further purified by chromatography, finally yielding the title compound as a yellow oil.

EXAMPLE 89

5-(S,R)-Hydroxy-6-(R,S)-(2-furylmethanthio)-8-phenyl-7(E,Z)-octenoic acid

This compound was prepared by the method described in Example 88, employing furfuryl mercaptan in place of dimethylmercaptosuccinate and 2 molar sodium carbonate in place of 0.1 molar potassium carbonate.

EXAMPLE 90

(a)
Methyl-5,6-(E)-oxido-8-(1-naphthyl)-7-(E,Z)-octenoate

To a stirred suspension of 1-naphthylmethyl triphenyl phosphonium chloride (41.37 g) in dry tetrahydrofuran (700 ml) under nitrogen at −70° C. was added n-butyl lithium (59 ml, 1.6 molar solution in hexane). A deep orange colour developed immediately. After stirring the mixture at −70° C. for 15 minutes, a solution of methyl-5,6-(E)-oxido-6-formyl-hexanoate (16.23 g) in dry tetrahydrofuran (50 ml) was added, and the reaction mixture allowed to warm gradually to room temperature (accompanied by partial discharge of ylid coloration to final straw yellow colour). Stirring at room temperature was continued for a further 90 minutes, when the reaction was shown to be complete by tlc.

The reaction mixture was evaporated in vacuo and extracted (3 times) with diethyl ether. The extracts were evaporated to yield an amber oil which was purified by chromatography (hexane 50% diethyl ether on silica) to give the title compound as a light-yellow oil.

(b)
5-(S,R)-Hydroxy-6-(R,S)-(4-chlorophenylthio)-8-(1-naphthyl)-7-(E,Z)-octenoic acid To methyl-5,6-(E)-oxido-8-(1-naphthyl)-7-(E,Z)-octenoic, (100 mg) prepared as described in (a) above, and a trace of hydroquinone, under nitrogen, was added a mixture of triethylamine (103 μl), 4-chlorothiophenol (100 mg) and dry methanol (100 μl), also under nitrogen.

The reaction mixture was allowed to stand at room temperature for 48 hours and then blown down under a nitrogen stream, the residual oil being purified by chromatography (silica; eluent:dichloromethane) to give the methyl ester of the title compound as a yellow oil.

The above oil (50 mg) was stirred in methanol (1.5 ml) with 2 molar sodium carbonate solution (0.35 ml) and a trace of hydroquinone for 72 hours at room temperature and then 2 hours at 45° C. The reaction mixture was acidified with 1 molar hydrochloric acid and extracted with chloroform to give an oil which was purified by chromatography (silica; eluent:chloroform 10% methanol) to give the title compound as a pale yellow oil.

EXAMPLE 91

5-(S,R)-Hydroxy-6-(R,S)-(2-carboxyethylthio)-8-(1-naphthyl)-7-(E,Z)-octenoic acid This compound was prepared as in Example 78(b) with the epoxide of Example 90(a) and methyl-3-mercaptopropionate.

EXAMPLE 92

(a)
Methyl-5,6-(E)-oxido-8-(2-naphthyl)-7-(E,Z)-octenoate

This compound was prepared by the method of Example 90(a) using 2-naphthylmethyltriphenyl phosphonium chloride.

(b)
5-(S,R)-Hydroxy-6-(R,S)-(4-chlorophenylthio)-8-(2-naphthyl)-7-(E,Z)-octenoic acid.

This compound was prepared according to the method of Example 90(b), but employing the epoxide of (a) above.

EXAMPLE 93

5-(S,R)-Hydroxy-6-(R,S)-(methyl-N-trifluoroacetyl-cysteinyl)-8-(2-naphthyl)-7-(E,Z)-octenoic acid.

This compound was prepared by the method of Example 88(b) with the epoxide of Example 92(a) and methyl-N-trifluoroacetyl cysteine, and omitting the hydrolysis step.

EXAMPLE 94

5-(S,R)-Hydroxy-6-(R,S)-(cysteinyl)-8-(2-naphthyl)-7-(E,Z)-octenoic acid

This compound was prepared by the hydrolysis of the compound of Example 93, by the method described in Example 88(b).

EXAMPLE 95

(a) Methyl-5,6-(E)-oxido-9-phenyl-7-(Z)-nonenoate

This compound was prepared by the method described in Example 90(a) employing phenylethyltriphenyl phosphonium bromide.

(b)
5-(S,R)-Hydroxy-6-(R,S)-(4-chlorophenylthio)-9-phenyl-7-(Z)-nonenoic acid

This compound was prepared by the method of Example 90(b) with the epoxide of Example 95(a) and 4-chlorothiophenol.

EXAMPLE 96

5-(S,R)-Hydroxy-6-(R,S)-(2-furylmethanthio)-9-phenyl-7-(Z)-nonenoic acid

This compound was prepared by the method of Example 88(b) with the epoxide of Example 95(a).

EXAMPLE 97

(a) Methyl-5,6-(E)-oxido-13-phenyl-7-(Z)-tridecanoate

This compound was prepared by the method of Example 88(a) using phenylhexyltriphenylphosphonium bromide.

(b) 5-(S,R)-Hydroxy-6-(R,S)-(4-chlorophenylthio)-13-phenyl-7-(Z)-tridecenoic acid, sodium salt The corresponding acid of the title compound was prepared by the method of Example 88(b) using the compound of (a) above and 4-chlorothiophenol. The acid, however, was found to form appreciable amount of the δ-lactone and hence was converted to the sodium salt by the following procedure.

5-(S,R)-Hydroxy-6-(R,S)-(4-chlorophenylthio)-13-phenyl-7-(Z)-tridecenoic acid (170 mg) was added to 2M sodium bicarbonate solution (190 μl, 1 equivalent). The mixture was ultrasonicated and allowed to stand at room temperature for 24 hours, to give the title compound in aqueous solution.

EXAMPLE 98

5-(S,R)-Hydroxy-6-(R,S)-(2-furylmethanthio)-13-phenyl-7-(Z)-tridecenoic acid, sodium salt This compound was prepared according to the method of Example 88(b) using the epoxide of Example 97(a) and conversion to the sodium salt as in Example 97(b).

EXAMPLE 99

5-(S,R)-Hydroxy-6-(R,S)-cysteinyl-13-phenyl-7-(Z)-tridecenoic acid

This compound was prepared by the method of Example 88(b) employing the epoxide from Example 97(a) and methyl-N-trifluoroacetyl cysteine.

EXAMPLE 100

(a) 2-Hydroxy-4-mercapto-acetophenone

This thiol was prepared from the corresponding dihydroxy compound by the method of Newman and Karnes (J.O.C. 31 3980-4 (1966).

2,4-Dihydroxyacetophenone (68.4 g), potassium carbonate (68.31 g) and dimethylthiocarbamoyl chloride (65.63 g) in dry acetone (1200 ml) were stirred at room temperature for 2 hours and then refluxed over night. The reaction mixture was poured into water (1500 ml), stirred, filtered and dried in vacuo to give 0-(4-acetyl-3-hydroxyphenyl)-N,N-dimethylthiocarbamate as a white solid, m.p. 150° to 152° C.

The above compound was added as a powder in one portion to boiling diphenylether (1600 ml) and refluxing was continued for a further 20 minutes under nitrogen. The diphenyl ether was evaporated in vacuo and the residue boiled in carbon tetrachloride solution was decolourising charcoal for 30 minutes. Filtration and evaporation of the filtrates gave S-(4-acetyl-3-hydroxyphenyl)-N,N-dimethylthiocarbamate as a light-brown crystalline solid, m.p. 124° to 126° C.

The above compound was heated to boiling in 10% sodium hydroxide solution and a milky $H_2O/Ph_2O$ mixture distilled off until all diphenyl ether removed. The mixture was then cooled, methanol (2000 ml) added and the suspension refluxed over night. The methanol was evaporated in vacuo, the aqueous layer extracted (2×) with diethyl ether (extracts discarded) and then acidified with 5M HCl (340 ml). The acid aqueous layer was then extracted with diethyl ether (2×), the combined extracts washed with water, dried over $MgSO_4$, filtered and evaporated. The residue was purified by column chromatography (silica; eluent 100% $CHCl_3$) and treatment with decolourising charcoal in boiling carbon tetrachloride to give the title compound as a light-yellow crystalline solid, m.p. 70° to 72° C.

(b) 2-Hydroxy-3-n-propyl-4-mercapto-acetophenone

This thiol was prepared by the method of (a) above, employing 2,4-dihydroxy-3-n-propyl-acetophenone.

(c) 5-(S,R)-Hydroxy-6-(R,S)-(2-n-propyl-3-hydroxy-4-acetylphenylthio)-9-phenyl-7-(Z)-nonenoic acid This compound was prepared by the method of Example 78(b) employing the epoxide of Example 95(a) and 2-hydroxy-3-n-propyl-4-mercaptoacetophenone (prepared as in (a) above).

EXAMPLE 101

5-(S,R)-Hydroxy-6-(R,S)-(3-hydroxy-4-acetylphenylthio)-9-phenyl-7-(Z)-nonenoic acid This compound was prepared by the method of Example 88(b) employing the epoxide of Example 95(a) and 2-hydroxy-4-mercaptoacetophenone (prepared as in Example 100(a)).

EXAMPLE 102

5-(S,R)-hydroxy-6-(R,S)-(3-hydroxy-4-acetylphenylthio)-13-phenyl-7-(Z)-tridecenoic acid This compound was prepared by the method of Example 88(b) employing the epoxide of Example 97(a) and 2-hydroxy-4-mercaptoacetophenone from Example 100(a).

EXAMPLE 103

(RR,SS) 6-(1-Phenylsulphinyl-3-phenylpropyl)-tetrahydro-2H-pyran-2-one (1-Phenylthio-3-phenylpropyl)-tetrahydro-2H-pyran-2-one, obtained as in Example 1(c), was oxidised using 1 equivalent of oxidising agent (m-chloroperoxybenzoic acid) as described in Example 16 to afford (RR,SS) 6-(1-phenylsulphinyl-3-phenylpropyl)tetrahydro-2H-pyran-2-one as a viscous oil (78%).

Typical formulations are prepared, employing one or more of the active compounds of the inventions as follows:

EXAMPLE 104

| Capsules | |
|---|---|
| Active ingredient | 5 mg |
| Starch flowable | 200 mg |
| Silicone fluid | 5 mg |

-continued

| Capsules | |
|---|---|
| | 210 mg |

The active ingredient was mixed with part of the starch and combined with the remainder of the starch previously mixed with silicone fluid and filled into hard gelatin capsules.

EXAMPLE 105

| Tablets | |
|---|---|
| Active ingredient | 10 mg |
| Fumed silica | 50 mg |
| Microcrystalline cellulose | 200 mg |
| Polyvinyl pyrrolidone | 20 mg |
| Sodium carboxymethyl starch | 20 mg |
| Magnesium stearate | 6 mg |
| | 306 mg |

Fumed silica and the active ingredient were mixed together and microcrystalline cellulose added. The whole was massed with a solution of polyvinyl pyrrolidone in water. The mass was passed through a screen, dried, sized and mixed with the sodium carboxymethyl starch and magnesium stearate prior to compression in a tablet machine to yield tablets weighing 306 mg.

EXAMPLE 106

| Suspensions | |
|---|---|
| Active ingredient | 5 mg |
| Sodium carboxymethyl cellulose | 100 mg |
| Sucrose | 1.25 g |
| p-Hydroxybenzoate | 0.5 mg |
| Flavour | q.s. |
| Colour | q.s. |
| Purified water to | 5.0 ml |

The sucrose was dissolved in part of the water and the sodium carboxymethyl cellulose added to form a smooth paste. The p-hydroxybenzoate and colour was dissolved in part of the water and added to the sucrose solution. The active ingredient was passed through a sieve into the aqueous solution and the flavour and sufficient water added to make up to volume.

EXAMPLE 107

| Aerosols | |
|---|---|
| Active ingredient | 5 mg |
| Ethanol | 30 ml |
| Propellent 11/114 | q.s. |

The active ingredient was dissolved in ethanol, filled into glass bottles, sealed with valve (metered 0.01 ml) and charged with mixed propellent.

We claim:

1. A compound of the formula

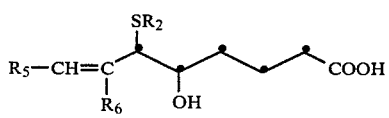

in which $R_2$ is alkyl, cycloalkyl or alkenyl of up to 10 carbon atoms, unsubstituted or substituted by one or more substituents selected from aryl, cycloalkyl, halogen, hydroxy, $NHR_3$, and $COX$, where $R_3$ is H, $C_{1-4}$ alkyl, aryl, or $COX'$, X is OH, OR', or $NH_2$, X' is $C_{1-4}$ alkyl or $NH_2$, and R' is $C_{1-4}$ alkyl, $R_5$ is $C_{10-14}$ alkyl or $R_7CH=CH$—, where $R^7$ is $C_{8-12}$ alkyl, phenyl, or naphthyl, and $R_6$ is H or $C_{1-4}$ alkyl, or pharmaceutically acceptable salts, esters, or internal lactones thereof.

2. A compound according to claim 1 in which $R_2$ is of the formula

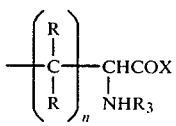

where each R is independently H or $C_{1-4}$ alkyl and n is 1 to 3, X is OH or OR' and $R_3$ is H or COR" where each of R' and R" is independently $C_{1-4}$ alkyl.

3. A compound according to claim 2 of the formula

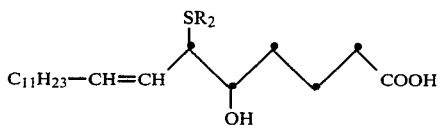

in which $R_2$ is

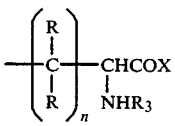

where each R is independently H or $C_{1-4}$ alkyl and n is 1 to 3, X is OH or OR' and $R_3$ is H or COR" where each of R' and R" is independently $C_{1-4}$ alkyl.

4. A compound of the formula

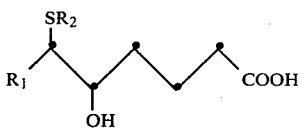

in which $R_1$ is substituted or unsubstituted phenyl or naphthyl or a group of the formula $R_5$—CH=CH— where $R_5$ is phenyl, benzyl or naphthyl, and $R_2$ is unsubstituted or substituted phenyl; and the lactone, salt and ester forms thereof.

5. A compound according to claim 4 in which $R_1$ is naphthyl and $R_2$ is phenyl substituted with 1 to 3 halogen, nitro or trifluoromethyl groups.

6. A compound of the formula

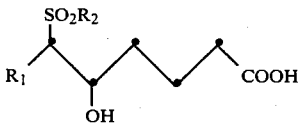

in which $R_1$ is a group of formula $R_5$—CH=CH— or $R_5$—$CH_2CH_2$— where $R_5$ is phenyl and $R_2$ is unsubstituted or substituted $C_{1-4}$ alkyl or unsubstituted or substituted phenyl; and the lactone, salt and ester forms thereof.

7. The compound of claim 3 which is 5(S)-hydroxy-6(R)-[(2-(N-acetylamino)-2-methoxycarbonyl-1-ethyl-1-methylethyl)thio]-7(Z)-nonadecenoic acid.

8. A pharmaceutical composition useful in the treatment of allergic or inflammatory disorders comprising an effective amount of a compound according to claim 1 in association with a pharmaceutically acceptable diluent or carrier.

9. A method of treating an allergic/inflammatory disorder which comprises administering an effective amount of a compound according to claim 1.

* * * * *